(12) United States Patent
Plettenburg et al.

(10) Patent No.: US 8,742,116 B2
(45) Date of Patent: Jun. 3, 2014

(54) CYCLOALKYLAMINE SUBSTITUTED ISOQUINOLONE DERIVATIVES

(75) Inventors: Oliver Plettenburg, Frankfurt am Main (DE); Armin Hofmeister, Frankfurt am Main (DE); Katrin Lorenz, Frankfurt am Main (DE); Joachim Brendel, Bad Vibel (DE); Matthias Löhn, Frankfurt am Main (DE); John Weston, Frankfurt am Main (DE)

(73) Assignee: Sanofi, Paris (FR)

( * ) Notice: Subject to any disclaimer, the term of this patent is extended or adjusted under 35 U.S.C. 154(b) by 1238 days.

(21) Appl. No.: 12/487,479

(22) Filed: Jun. 18, 2009

(65) Prior Publication Data
US 2010/0056518 A1   Mar. 4, 2010

Related U.S. Application Data

(63) Continuation of application No. PCT/EP2007/011164, filed on Dec. 19, 2007.

(30) Foreign Application Priority Data

Dec. 27, 2006   (EP) .................................. 06026899

(51) Int. Cl.
   *A61K 31/445*   (2006.01)
   *C07D 211/32*   (2006.01)
(52) U.S. Cl.
   USPC .......................................... 546/199; 514/322
(58) Field of Classification Search
   None
   See application file for complete search history.

(56) References Cited

U.S. PATENT DOCUMENTS

| | | | |
|---|---|---|---|
| 5,480,883 A | 1/1996 | Spada et al. |
| 6,903,107 B1 | 6/2005 | Timmers et al. |
| 7,217,722 B2 | 5/2007 | Takami et al. |
| 7,618,985 B2 | 11/2009 | Ray et al. |
| 2003/0220368 A1 | 11/2003 | Ozaki et al. |
| 2004/0138286 A1 | 7/2004 | Imazaki et al. |
| 2006/0079556 A1 | 4/2006 | Sher et al. |
| 2007/0060595 A1 | 3/2007 | Yoshizawa et al. |
| 2008/0045566 A1 | 2/2008 | Ray et al. |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087829 | 4/1998 |
| WO | 9202476 | 2/1992 |
| WO | 9706802 | 2/1997 |
| WO | 9723214 | 7/1997 |
| WO | WO 98/06433 | 2/1998 |
| WO | 9911642 | 3/1999 |
| WO | 0024718 | 5/2000 |
| WO | 0073299 | 12/2000 |
| WO | WO 01/39726 | 6/2001 |
| WO | 0153288 | 7/2001 |
| WO | 0156988 | 8/2001 |
| WO | 0164238 A2 | 9/2001 |
| WO | 0164656 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | WO 03/053330 | 7/2003 |
| WO | 2004113297 | 12/2004 |
| WO | WO 2004/106325 | 12/2004 |
| WO | 2005035933 | 2/2005 |
| WO | 2005035516 | 4/2005 |
| WO | WDO 2005/030791 | 4/2005 |
| WO | WO 2005/030130 | 4/2005 |
| WO | 2005054202 | 6/2005 |
| WO | 2005074535 | 8/2005 |
| WO | 2005087226 | 9/2005 |
| WO | 2005095362 | 10/2005 |
| WO | 2007012421 A1 | 2/2007 |
| WO | WO 2007/012422 | 2/2007 |
| WO | WO 2007012422 A1 * | 2/2007 |
| WO | 2007039563 A1 | 4/2007 |

(Continued)

OTHER PUBLICATIONS

Patani, G. et al., Chem. Rev. 1996, vol. 96, pp. 3147-3176.*
U.S. Appl. No. 11/961,193, filed Dec. 20, 2007, Plettenburg et. al.
U.S. Appl. No. 12/019,866, filed Jan. 25, 2008, Plettenburg et. al.
U.S. Appl. No. 12/019,799, filed Jan. 25, 2008, Plettenburg et. al.
U.S. Appl. No. 12/487,403, filed Jun. 18, 2009, Plettenburg et. al.
U.S. Appl. No. 12/487,455, filed Jun. 18, 2009, Plettenburg et. al.
U.S. Appl. No. 12/487,525, filed Jun. 18, 2009, Plettenburg et. al.
U.S. Appl. No. 12/487,386, filed Jun. 18, 2009, Plettenburg et. al.

(Continued)

*Primary Examiner* — Heidi Reese
(74) *Attorney, Agent, or Firm* — Scully, Scott, Murphy & Presser, P.C.

(57) ABSTRACT

The invention relates to 6-substituted isoquinolone derivatives of the formula (I)

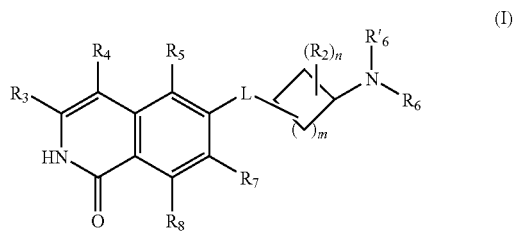

useful for the treatment and/or prevention of diseases associated with Rho-kinase and/or Rho-kinase mediated phosphorylation of myosin light chain phosphatase, and compositions containing such compounds.

47 Claims, No Drawings

(56) References Cited

FOREIGN PATENT DOCUMENTS

| | | |
|---|---|---|
| WO | WO 2007/065916 | 6/2007 |
| WO | 2008020081 A1 | 2/2008 |
| WO | WO 2008/020081 | 2/2008 |
| WO | WO 2008020081 A1 * | 2/2008 |
| WO | 2008077555 A2 | 7/2008 |
| WO | 2008077556 A1 | 7/2008 |

OTHER PUBLICATIONS

U.S. Appl. No. 12/487,409, filed Jun. 18, 2009, Plettenburg et. al.
U.S. Appl. No. 12/487,503, filed Jun. 18, 2009, Plettenburg et. al.
Yoshii, A., et. al., Relaxation of Contracted Rabbit Tracheal and Human Bronchial Smooth Muscle by Y-27632 Through Inhibition of Ca2+ Sensitization, Am. J. Resp. Cell Mol. Biol., vol. 20, pp. 1190-1200, (1999).
Zhou, Y., et. al., Nonsteroidal Anti-inflammatory Drugs Can Lower Amyloidogenic AB42 by Inhibiting Rho, Science, vol. 302, pp. 1215-1217, (2003).
Al, S., et. al., Rho-Rho Kinase Is Involved in Smooth Muscle Cell Migration Through Myosin Light Chain Phosphorylation-Dependent and Independent Pathways, Atherosclerosis, vol. 155, pp. 321-327, (2001).
Amano, M., et. al., Formation of Actin Stress Fibers and Focal Adhesions Enhanced by Rho-Kinase, Science, vol. 275, pp. 1308-1311, (1997).
Bauer, M., et. al., Dichotomous Regulation of Myosin Phosphorylation and Shape Change by Rho-Kinase and Calcium in intact Human Platelets, Blood, vol. 94, No. 5, (1999), pp. 1665-1672.
Chellaiah, M., et. al.,, Rho-Dependent Rho Kinase Activation increases CD44 Surface Expression and Bone Resorption in Osteoclasts, The Journal of Biological Chemistry. vol. 278, No. 31, (2003), pp. 29086-29097.
Chitaley, K., et. al., Antagonism of Rho-Kinase Stimualates Rat Penile Erection Via a Nitric Oxide-Independent Pathway, Nature Medicine, vol. 7, No. 1, (2001), pp. 119-122.
Demiryurek. S., et. al., Effects of Fasudil, a Rho-Kinase Inhibitor, On Myocardial Preconditioning in Anesthetized Rats, European Journal of Pharmacology. vol. 527, (2005), pp. 129-140.
Fukumoto, V., et. al., Acute Vasodilator Effects of a Rho-Kinase Inhibitor, Fasudil, in Pateients With Severe Pulmonary Hypertension, Heart, (2005), vol. 91, pp. 391-392.
Furukawa, N., et. al., Role of Rho-Kinase in Regulation of Insulin Action and Glucose Homeostasis, Cell Metabolism, vol. 2, pp. 119-129, (2005).
Gingras, D., et. al., Tyrosine Phosphorylation of the Vascular Endothelial-Growth-Factor Receptor-2 (VEGFR-2) is Modulated by Rho Proteins, Biochem. J., (2000), vol. 348, pp. 273-280.
Gokina, N. I., et. al., Effects of Rho Kinase Inhibition on Cerebral Artery Myogenic Tone and Reactivity, J. Appl. Physiol. vol. 98, pp. 1940-1948, (2005).
Hara, M., et. al., Protein Kinase inhibition by Fasudil Hydrochloride Promotes Neurological Recovery After Spinal Cord injury in Rats, J Neurosurg. (Spine 1), vol. 93, pp. 94-101, (2000).
Hattori, T., et. al., Long-Term inhibition of Rho-Kinase Suppresses Left Ventricular Remodeling After Myocardial Infarction in Mice, Circulation, (2004), vol. 109, pp. 2234-2239.
Okada, H., et. al., Synthesis and Antitumor Activities of Prodrugs of Benzoylphenylureas, Chem. Pharm. Bull (1994), pp. 57-61, vol. 42, No. 1.
Hitomi, A., et. al., Hemorheological Abnormalities in Experimental Cerebral Ischemia and Effects of Protein Kinase Inhibitor on Blood Fluidity, Life Sciences, vol. 67, (2000), pp. 1929-1939.
Honjo, M., et. al., Effects of Rho-Associated Protein Kinase Inhibitors Y-27632 on Intraocular Pressure and Outflow Facitlity, Investigative Ophthalmology & Visual Science, (2001), vol. 42, No. 1 , pp. 137-144.
Inoue, M., et, al., Initiation of Neuropathic Pain Requires Lysophospatidic Acid Receptor Signaling, Nature Medicine, vol. 10, No. 7, pp. 712-718, (2004).
Itoh, et. al., An Essential Part for Rho-Associated Kinase in the Transcellular Invasion of Tumor Cells, Nature Medicine, vol. 5, No. 2, pp. 221-225, (1999).
Kawaguchi, A., et. al., The Effect of a Rho Kinase Inhibitor Y-27632 on Superoxide Production, Aggregation and Adhesion in Human Polymorphonuclear Leukocytes, European Journal of Pharmacology, vol. 403, (2000), pp. 203-208.
Kim, I., et. al., Thin and Thick Filament Regulation of Contractility in Experimental Cerebral Vasospasm, Neurosurgery, vol. 46, No. 2, (2000), pp. 440-447.
Kimura, K., et. al., Regulation of the Association of Adducin with Actin Filaments by Rho-Associated Kinase (Rho-Kinase) and Myosin Phosphatase, The Journal of Biological Chemistry, vol. 273, No. 10, pp. 5542-5548, (1998).
Kish, T., et. al., Rho-Kinase Inhibitor Improves Increased Vascular Resistance and Impaired Vasodilation of the Forearm in Patients With Heart Failure, Circulation, (2005), vol. 111, pp. 2741-2747.
Klages, B., et. al., Activation of G12/G13 Results in Shape Change and Rho/Rho-Kinase-Mediated Myosin Light Chain Phosphorylation in Mouse Platelets, The Journal of Cell Biology, vol. 144, No. 4, (1999), pp. 745-754.
Lin, T., et. al., Rho-ROCK-LIMK-Cofilin Pathway Regulates Shear Stress Activation of Sterol Regulatory Element Binding Proteins, Circulation Research, (2003), vol. 92, pp. 1296-1304.
Maruoka, S., et. al., Elastase Anti-Elastase Imbalance in the Pathogenesis of COPD, Nippon Rinsho, (1999), vol. 57, pp. 1982-1987.
Masumoto, A. et. al., Suppression of Coronary Artery Spasm by the Rho-Kinase Inhibitor Fasudil in Patients With Vasospastic Angina, Circulation, (2002), vol. 105, pp. 1545-1547.
Nakahara, T., et. al., Y-27632 Potentiates Relaxant Effects of B2-Adrenoceptor Agonists in Bovine Tracheal Smooth Muscle, European Journal of Pharmacology, vol. 389, (2000), pp. 103-106.
Negoro, N., et. al., The Kinase Inhibitor Fasudil (HA-1077) Reduces intimal Hyperplasia through Inhibiting Migration and Enhancing Cell Loss of Vascular Smooth Muscle Cells, Biochemical and Biophysical Research Communications, vol. 262, pp. 211-215, (1999).
Noma, K. et. al., Physiological Role of ROCKS in the Cardiovascular System, Am. J. Physiol. Cell Physiol., vol. 290, pp. C661-C668, (2006).
Pacaud, P., et. al., Rho Proteins and Vascular Diseases, Archives Des Maladies Du CCeur Et Des Vaisseaux, vol. 98, pp. 249-254, (2005).
Pommereau, A., et. al., Two Simple and Generic Antibody-Independent Kinase Assays: Comparison of a Bioluminescent and a Microfluidic Assay Format, J. Biomol Screen, (2004). vol. 9, pp. 409-416.
Retzer, M., et. al., Lysophosphatidic Acid-Induced Platelet Shape Change Proceeds Via Rho/Rho Kinase-Mediated Myosin Light-Chain and Moesin Phosphorylation, Cellular Signaliing, vol. 12, pp. 645-648, (2000).
Retzer, M., et. al., Mildly Oxidised Low Density Lipoprotein Induces Platelet Shape Change Via Rho-Kinase-Dependent Phosphorylation of Myosin Light Chain and Moesin, FEBS Letters, vol. 466, pp. 70-74, (2000).
Sandu, O. A., et. al., Diabetes in the Goto-Kakizaki Rat Is Accompanied by Impaired Insulin-Mediated Myosin-Bound Phosphatase Activation and Vascular Smooth Muscle Cell Relaxation, Diabetes, vol. 49, (2000), pp. 2175-2189.
Sato, M., et. al., Involvement of Rho-Kinase-Mediated Phosphorylation of Myosin Light Chain in Enhancement of Cersberal Vasospasm, Circulation Research, (2000), vol. 87, pp. 195-200.
Satoh, S.-I., et. al., Pharmacological Profile of Hydroxy Fasudil as a Selective Rho Kinase Inhitor on Ischemic Brain Damage, Life Sciences, vol. 69, (2001), pp. 1441-1453.
Seasholtz, T. M., et. al., Rho and Rho Kinase Mediate Thrombin-Stimulated Vascular Smooth Muscle Cell DNA Synthesis and Migration , Circulation Research, (1999), vol. 84, pp. 1186-1193.
Setoguchi, H., et. al., Leukotriene C4 Enhances the Contraction of Porcine Tracheal Smooth Muscle Through the Activation of Y-27632, a Rho Kinase Inhibitor, Sensitive Pathway, British Journal of Pharmacology, (2001), vol. 132, pp. 111-118.

(56) References Cited

OTHER PUBLICATIONS

Shimokawa, H., et. al., Anti-Anginal Effect of Fasudil, a Rho-Kinase Inhibitor, in Patients With Stable Effort Angina: A Multicenter Study, Journal of Cardiovascular Pharmacology, (2002), vol. 40, pp. 751-761.
Somlyo, A. V., et. al., Rho-Kinase Inhibitor Retards Migration and In Vivo Dissemination of Human Prostate Cancer Cells, Biochemical and Biophysical Research Communications, vol. 269, pp. 652-659, (2000).
Steioff, K., et. al., Long Term Rho-Kinase Inhibition Ameliorates Endothelial Dysfunction in LDL-Receptor Deficient Mice, European Journal of Pharmacology, vol. 512, (2005), pp. 247-249.
Tatsumi, S., et. al., Involvement of Rho-Kinase in Inflammatory and Neuropathic Pain Through Phosphorylation of Myristoylated Alainine-Rich C-Kinase Substrate (MARCKS), Neuroscience, vol. 131, pp. 491-498, (2005).
Totsukawa, G., et. al., Distinct Roles of ROCK (Rho-Kinase) and MLCK in Spatial Regulation of MLC Phosphorylation for Assembly of Stress Fibers and Focal Adhesions in 3T3 Fibroblasts, The Journal of Cell Biology, vol. 150, No. 4, pp. 797-806, (2000).
Uchida, S., et. al., The Suppression of Small GTPase Rho Signal Transduction Pathway Inhibits Angiogenesis in Vitro and in Vivo, Biochemical and Biophysical Research Communications, Vol, 269, pp. 633-640, (2000).
Uehata, M., et. al., Calcium Sensitization of Smooth Muscle Mediated by a Rho-Associated Protein Kinase in Hypertension, Nature, vol. 389, pp. 990-994, (1997).
Vicente-Manzanares, M., et. al., A Role for the Rho-p160 Rho Coiled-Coil Kinase Axis in the Chemokine Stromal Cell-Derived Factor-1a-induced Lymphocyte Actomyosin and Microtubular Organization and Chemotaxis, The Journal of Immunology, (2002), vol. 168, pp. 400-410.
Vicente-Manzanares, M., et. al., The RhoA Effector MDia is induced During T Cell Activation and Regulates Actin Polymerization and Cell Migration in T Lymphocytes, The Journal of Immunology, (2003), vol. 171, pp. 1023-1034.
Wakino, S., et. al., Rho/Rho Kinase as a Potential Target for the Treatment of Renal Disease, Drug News Perspective, (2005), vol. 18, pp. 639-643.
Yamakawa, T., et. al., Involvement of Rho-Kinase in Angiotensin II-Induced Hypertrophy of Rat Vascular Smooth Muscle Cells, Hypertension, (2000), vol. 35, pp. 313-318.
Yamamoto, Y., et. al., The Protein Kinase Inhibitor Fasudil Protects Against Ischemic Myocardial Injury Induced by Endothelin-1 in the Rabbit, Journal of Cardiovascular Pharmacology, vol. 35, pp. 203-211, (2000).
Yoshida, Y., et. al., Studies on Anti-*Helicobacter pylori* Agents. Part 1: Benzyloxyisoquinoline Derivatives, Bioorg. & Med. Chem., vol. 7 (1999), pp. 2647-2666.

Alvarez, M. et al., "Product Class 5: Isoquinolines" Science of Synthesis (2005) pp. 661-838, vol. 15.
Alvarez, M. et al., "Product Class 6: Isoquinolines" Science of Synthesis (2005) pp. 839-890, vol. 15.
Remington's Pharmaceutical Sciences 17th Edition (1985), p. 1418.
Forzato, C. et al., "Baker's yeast reduction of 4-hetero-2-(2-nitroethyl)cyclohexanones" Tetrahedron: Asymmetry (1997) pp. 1811-1820, vol. 8.
U.S. Appl. No. 12/970,376, filed Dec. 16, 2010, Inventor: Plettenburg, et al, entitled: "6-Substituted Isoquinolines and Isoquinolinones".
U.S. Appl. No. 13/000,754, filed Apr. 20, 2011, Inventor: Plettenburg et al., entitled: "Substituted Isoquinolines and Isoquinolinones as Rho Kinase Inhibitors".
U.S. Appl. No. 13/000,202, filed Dec. 20, 2010, Inventor: Plettenburg et al., entitled: "Bi-and Polycyclic Substituted Isoquinoline and Isoquinolinone Derivatives".
Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.
Takami, A. et al., "Design and Synthesis of Rho Kinase Inhibitors (I)" Bioorganic & Medicinal Chemistry (2004) pp. 2115-2137, vol. 12.
Iwakubo, M. et al., "Design and Synthesis of Rho Kinase Inhibitors (III)" Bioorganic & Medicinal Chemistry (2007) pp. 1022-1033, vol. 15.
Iwakubo, M. et al., "Design and Synthesis of Rho Kinase Inhibitors (II)" Bioorganic & Medicinal Chemistry (2007) pp. 350-364, vol. 15.
Tamura, M. et al., "Development of Specific Rho-Kinase Inhibitors and Their Clinical Application" Biochimicia et Biophysica Acta (2005) pp. 245-252, vol. 1754.
Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.
Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.
Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.
Caron, S. et al., "The Synthesis of a Selective PDE4/TNFα Inhibitor" Organic Process Research and Development (2001) pp. 587-592, vol. 5.
Curran, T.T., et al., "The Preparation of Optically Active 2-Cyclopentan-1,4-Diol Derivatives from Furfuryl Alcohol", Tetrahedron, pp. 1983-2004, vol. 53(6), Feb. 10, 1997.

* cited by examiner

CYCLOALKYLAMINE SUBSTITUTED ISOQUINOLONE DERIVATIVES

FIELD OF THE INVENTION

The present invention relates to novel isoquinolone derivatives as described in the claims, their preparation and their use in the treatment and/or prevention of diseases related to the inhibition of Rho-kinase and/or of Rho-kinase mediated phosphorylation of myosin light chain phosphatase.

BACKGROUND OF THE INVENTION

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-1948), bronchial smooth muscle contraction (Yoshii et al. Am. J. Resp. Cell Mol. Biol. 20, 1190-1200), asthma (Setoguchi et al. Br J. Pharmacol. 2001, 132, 111-118; Nakahara, et al. Eur J 2000, 389, 103) and chronic obstructive pulmonary disease (COPD, Maruoka, Nippon Rinsho, 1999, 57, 1982-1987), hypertension, pulmonary hypertension (Fukumoto et al. Heart, 91, 391-392, 2005, Mukai et al. Nature 1997, 389, 990-994) and ocular hypertension and regulation of intraocular pressure (Honjo et al. Invest. Opthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-1547, Shimokawa et al. JCP, 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-643), myocardial infarction (Demiryurek et al. Eur J. Pharmacol. 2005, 527, 129-140, Hattori et al. Circulation, 2004, 109, 2234-2239), cardiac hypertrophy and failure (Yamakawa, et al. Hypertension 2000, 35, 313-318, Liao et al. Am J Physiol Cell Physiol. 2006, 290, C661-668, Kishi et al. Circ 2005, 111, 2741-2747), coronary heart disease, atherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu et al. Diabetes 2000, 49, 2178, Maeda et al. Cell Metab. 2005, 2, 119-129), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Hara et al. J Neurosurg 2000, 93, 94), cerebral ischemia (Uehata et al. Nature 1997, 389, 990; Satoh et al. Life Sci. 2001, 69, 1441-53; Hitomi et al. Life Sci 2000, 67, 1929; Yamamoto et al. J Cardiovasc. Pharmacol. 2000, 35, 203-211), cerebral vasospasm (Sato et al. Circ Res 2000, 87, 195; Kim et al. Neurosurgery 2000, 46, 440), pain, e.g. neuropathic pain (Tatsumi et al. Neuroscience 2005, 131, 491, Inoue et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh et al. Nature Medicine 1999, 5, 221; Somlyo, et al. Res Commun 2000, 269, 652), angiogenesis (Uchida et al. Biochem Biophys Res 2000, 269, 633-640; Gingras et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa et al. FEBS Lett. 2000, 466, 70-74; Bauer et al. Blood 1999, 94, 1665-1672, Klages et al. J Cell Biol 1999, 144, 745; Retzer et al. Cell Signal 2000, 12, 645) and leukocyte aggregation (Kawaguchi et al. Eur J. Pharmacol. 2000, 403, 203-208; Sanchez-Madrid et al. J. Immunol. 2003, 171, 1023-1034, Sanchez-Madrid et al. J. Immunol. 2002, 168, 400-410), and bone resorption (Chellaiah et al. J Biol. Chem. 2003, 278, 29086-29097). Na/H exchange transport system activation (Kawaguchi et al. Eur J. Pharmacol. 2000, 403, 203-208), Alzheimer's disease (Zhou et al. Science 2003, 302, 1215-1217), adducin activation (Fukata et al. J. Biol. Chem. 1998, 273, 5542-5548), and in SREB (Sterol response binding element) signalling and its effects on lipid metabolism (Lin et al. Circ. Res. 2003, 92, 1296-1304).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a —$(CH_2)_{1-6}$—O—$(CH_2)_{0-6}$—, a —$(CH_2)_{0-6}$—S—$(CH_2)_{0-6}$— or a —$(CH_2)_{0-6}$-linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes —O—$(C_0$-$C_{10})$ alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[($C_1$-$C_6$)alkylene)]$_{0-1}$-Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I—X—Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}R^{52}$, wherein $R^{51}$ and $R^{52}$ may be hydrogen, ($C_1$-$C_6$) alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}R^{52}$, wherein $R^{51}$ and $R^{52}$ may be hydrogen, ($C_1$-$C_6$)alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 03/053330 (Ube) generically describes isoquinolone derivatives of the formula

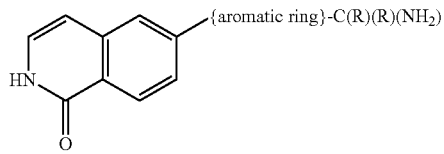

as Rho-kinase inhibitors.

SUMMARY OF THE INVENTION

An embodiment of the present invention is a compound of the formula (I)

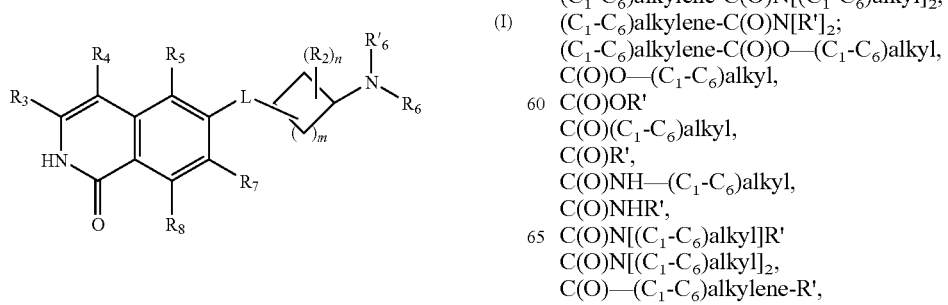

wherein
$R_2$ is H, halogen or ($C_1$-$C_6$)alkyl;
$R_3$ is
H,
halogen,
($C_1$-$C_6$)alkyl,
($C_1$-$C_6$)alkylene-R',
OH,
O—R",
$NH_2$,
NHR",
NR"R" or
NH—C(O)—R",
$R_4$ is
H,
halogen,
hydroxy,
CN,
($C_1$-$C_6$)alkyl,
R',
($C_1$-$C_6$)alkylene-R';
$R_5$ is
H,
halogen,
CN,
$NO_2$,
($C_1$-$C_6$)alkyl,
($C_2$-$C_6$)alkenyl,
R',
($C_1$-$C_6$)alkylene-($C_6$-$C_{10}$)aryl,
($C_2$-$C_6$)alkenylene-($C_6$-$C_{10}$)aryl,
($C_1$-$C_6$)alkylene-($C_5$-$C_{10}$)heterocyclyl,
CH(OH)—($C_1$-$C_6$)alkyl,
$NH_2$,
NH—R',
NH—$SO_2H$,
NH—$SO_2$—($C_1$-$C_6$)alkyl,
NH—$SO_2$—R',
NH—C(O)—($C_1$-$C_6$)alkyl,
NH—C(O)—R',
C(O)N[($C_1$-$C_6$)alkyl]$_2$,
C(O)OH, or
C(O)O—($C_1$-$C_6$)alkyl;
$R_6$ and $R_6$' are independently of each other
H,
R',
($C_1$-$C_8$)alkyl,
($C_1$-$C_6$)alkylene-R',
($C_1$-$C_6$)alkylene-O—($C_1$-$C_6$)alkyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)$NH_2$,
($C_1$-$C_6$)alkylene-C(O)NH—R',
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)N[R']$_2$;
($C_1$-$C_6$)alkylene-C(O)O—($C_1$-$C_6$)alkyl,
C(O)O—($C_1$-$C_6$)alkyl,
C(O)OR'
C(O)($C_1$-$C_6$)alkyl,
C(O)R',
C(O)NH—($C_1$-$C_6$)alkyl,
C(O)NHR',
C(O)N[($C_1$-$C_6$)alkyl]R'
C(O)N[($C_1$-$C_6$)alkyl]$_2$,
C(O)—($C_1$-$C_6$)alkylene-R', C(O)O($C_1$-$C_6$)alkylene-R',
or $R_6$ and $R_6'$, together with the N-atom to which they are attached, form a ($C_5$-$C_{10}$) heterocyclyl group;
$R_7$ is
H,
halogen,
CN,
$NO_2$,
($C_1$-$C_6$)alkyl,
O—($C_1$-$C_6$)alkyl,
($C_2$-$C_6$)alkenyl,
R',
($C_2$-$C_6$)alkenylene-($C_6$-$C_{10}$)aryl,
($C_1$-$C_6$)alkylene-R',
CH(OH)—($C_1$-$C_6$)alkyl,
$NH_2$,
NH—R',
NH—$SO_2$H,
NH—$SO_2$—($C_1$-$C_6$)alkyl,
NH—$SO_2$—R',
$SO_2$—$NH_2$,
$SO_2$—NHR',
NH—C(O)—($C_1$-$C_6$)alkyl,
NH—C(O)—R',
C(O)N[($C_1$-$C_6$)alkyl]$_2$,
C(O)OH, or
C(O)O—($C_1$-$C_6$)alkyl;
$R_8$ is H, halogen or ($C_1$-$C_6$)alkyl;
n is 1, 2, 3 or 4;
m is 1, 2, 3, 4 or 5,
L is O or O—($C_1$-$C_6$)alkylene;
R' is
($C_3$-$C_8$)cycloalkyl,
($C_5$-$C_{10}$)heterocyclyl,
($C_6$-$C_{10}$)aryl; and
R" is
($C_3$-$C_8$)cycloalkyl,
($C_5$-$C_{10}$)heterocyclyl,
($C_6$-$C_{10}$)aryl,
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R', or
($C_1$-$C_6$)alkylene-$NR_xR_y$;
$R_x$ and $R_y$ are independently of each other
($C_1$-$C_6$)alkyl,
($C_5$-$C_{10}$)heterocyclyl,
($C_6$-$C_{10}$)aryl,
($C_1$-$C_4$)alkylene-($C_5$-$C_{10}$)heterocyclyl,
($C_1$-$C_4$)alkylene-($C_6$-$C_{10}$)aryl,
($C_1$-$C_4$)alkylene-NH($C_1$-$C_6$)alkyl,
($C_1$-$C_4$)alkylene-N[($C_1$-$C_6$)alkyl]$_2$,
($C_1$-$C_4$)alkylene-N[($C_6$-$C_{10}$)aryl]$_2$, or
($C_1$-$C_4$)alkylene-N [($C_5$-$C_{10}$)heterocyclyl]$_2$;
wherein in residues $R_4$, $R_5$, $R_6$, $R_6'$, $R_7$ and $R_8$ as alkyl, alkylene or cycloalkyl can optionally be substituted one or more times by OH, $OCH_3$, COOH, $COOCH_3$, $NH_2$, $NHCH_3$, $N(CH_3)_2$, $CONHCH_3$ or $CON(CH_3)_2$;
wherein in residues $R_2$ to $R_8$ as alkyl or alkylene can optionally be substituted one or more times by halogen;
wherein in residues $R_3$ to $R_8$ as ($C_6$-$C_{11}$)aryl and ($C_5$-$C_{10}$) heterocyclyl are unsubstituted or substituted one or more times by a suitable group independently selected from OH, halogen, $NO_2$, $N_3$, CN, C(O)—($C_1$-$C_6$)alkyl, C(O)—($C_1$-$C_6$)aryl, COOH, COO($C_1$-$C_6$)alkyl, $CONH_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-OH, ($C_1$-$C_6$)alkylene-$NH_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, $PO_3H_2$, $SO_3H$, $SO_2$—$NH_2$, $SO_2NH$($C_1$-$C_6$)alkyl, $SO_2N$[($C_1$-$C_6$)alkyl]$_2$, S—($C_1$-$C_6$)alkyl, SO—($C_1$-$C_6$)alkyl, $SO_2$—($C_1$-$C_6$)alkyl, $SO_2$—N=CH—N[($C_1$-$C_6$)alkyl]$_2$, C(NH)($NH_2$), $NH_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—$SO_2$—($C_1$-$C_6$)alkyl, NH—$SO_2$—($C_6$-$C_{10}$)aryl, NH—$SO_2$—($C_5$-$C_{10}$)heterocyclyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl], ($C_6$-$C_{10}$)aryl, ($C_1$-$C_6$)alkylene-($C_6$-$C_{10}$)aryl, O—($C_6$-$C_{10}$)aryl, O—($C_1$-$C_6$)alkylene-($C_6$-$C_{10}$)aryl, ($C_5$-$C_{10}$)heterocyclyl, ($C_1$-$C_6$)alkylene-($C_5$-$C_{10}$)heterocyclyl, and O—($C_1$-$C_6$)alkylene-($C_5$-$C_{10}$)heterocyclyl, wherein the ($C_6$-$C_{10}$)aryl or ($C_5$-$C_{10}$)heterocyclyl in the substituent may be substituted one to three times by a group independently selected from halogen, OH, $NO_2$, CN, O—($C_1$-$C_6$)alkyl, ($C_1$-$C_6$)alkyl, $NH_2$, NH($C_1$-$C_6$)alkyl, N[($C_1$-$C_6$)alkyl]$_2$, $SO_2CH_3$, COOH, C(O)O—($C_1$-$C_6$)alkyl, $CONH_2$, ($C_1$-$C_6$)alkylene-O—($C_1$-$C_6$)alkyl, ($C_1$-$C_6$)alkylene-O—($C_6$-$C_{10}$)aryl, and O—($C_1$-$C_6$)alkylene-($C_6$-$C_{10}$)aryl; or wherein ($C_6$-$C_{10}$) aryl is vicinally substituted by a O—($C_1$-$C_4$)alkylene-O group whereby a 5-8-membered ring is formed together with the carbon atoms the oxygen atoms are attached to; and wherein aryl substituent of ($C_6$-$C_{10}$)aryl and ($C_5$-$C_{10}$) heterocyclyl substituent groups may not be further substituted by an aryl or heterocyclyl containing group;
and wherein, if m is 3, $R_6$ is not H, ($C_5$-$C_{10}$)heterocyclyl or ($C_6$-$C_{10}$)aryl; and
wherein, if m is 3 and $R_6$ is a residue selected from
($C_1$-$C_8$)alkyl,
($C_3$-$C_8$)cycloalkyl,
($C_1$-$C_6$)alkylene-R',
($C_1$-$C_6$)alkylene-O—($C_1$-$C_6$)alkyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)$NH_2$,
($C_1$-$C_6$)alkylene-C(O)NH—R', or
($C_1$-$C_6$)alkylene-C(O)N[R']$_2$;
alkyl, alkylene or cycloalkyl in said residue is substituted one or more times, preferably one to three times, by OH, $OCH_3$, COOH, $COOCH_3$, $NH_2$, $NHCH_3$, $N(CH_3)_2$, $CONHCH_3$ or $CON(CH_3)_2$; or
stereoisomeric form thereof and/or tautomeric form thereof and/or pharmaceutically acceptable salt thereof.

DETAILED DESCRIPTION OF THE INVENTION

Definitions
The terms ($C_1$-$C_2$)alkyl, ($C_1$-$C_4$)alkyl, ($C_1$-$C_6$)alkyl, ($C_1$-$C_8$)alkyl and the corresponding alkylene substituents are understood as a hydrocarbon residue which can be linear, i.e. straight-chain, or branched and has 1, 2, 3, 4, 5, 6, 7 or 8 carbon atoms, respectively. This also applies if an alkyl group occurs as a substituent on another group, for example in an alkoxy group (O-alkyl), S-alkyl or a —O—($C_1$-$C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may—if not otherwise stated—be halogenated once or more, e.g. alkyl groups may be fluorinated, e.g. perfluorinated. Examples of halogenated alkyl groups are $CF_3$ and $CH_2CF_3$, $OCF_3$, $SCF_3$, or $-O-(CF_2)_2-O-$.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Alkynyl are, for example, ethynyl, 1-propynyl, 2-propynyl (=propargyl) or 2-butynyl.

Halogen means fluoro, chloro, bromo or iodo.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A $(C_6-C_{10})$aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

A $(C_5-C_{10})$heterocyclyl group means a mono- or bicyclic ring system in which one or more carbon atoms can be replaced by one or more heteroatoms such as, for example 1, 2 or 3 nitrogen atoms, 1 or 2 oxygen atoms, 1 or 2 sulfur atoms or combinations of different heteroatoms. The heterocyclyl residues can be bound at any positions, for example on the 1-position, 2-position, 3-position, 4-position, 5-position, 6-position, 7-position or 8-position. $(C_5-C_{10})$heterocyclyl groups may be (1) aromatic [=heteroaryl groups] or (2) saturated or (3) mixed aromatic/saturated.

Suitable $(C_5-C_{10})$heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl. Substitutions in $(C_5-C_{10})$heterocyclyl residues can occur on free carbon atoms or on nitrogen atoms.

Preferred examples of $(C_5-C_{10})$heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl. A preferred $(C_5-C_{10})$heterocyclyl residue is a $(C_5-C_6)$heterocyclyl.

$(C_6-C_{10})$aryl and $(C_5-C_{10})$heterocyclyl groups are unsubstituted or, if not stated otherwise, substituted one or more times, preferably one to three times, by suitable groups independently selected from halogen, OH, $NO_2$, $N_3$, CN, $C(O)-(C_1-C_6)$alkyl, $C(O)-(C_1-C_6)$aryl, COOH, $COO(C_1-C_6)$alkyl, $CONH_2$, $CONH(C_1-C_6)$alkyl, $CON[(C_1-C_6)$alkyl$]_2$, $(C_3-C_8)$cycloalkyl, $(C_1-C_6)$alkyl, $(C_1-C_6)$alkylene-OH, $(C_1-C_6)$alkylene-$NH_2$, $(C_1-C_6)$alkylene-$NH(C_1-C_6)$alkyl, $(C_1-C_6)$alkylene-$N[(C_1-C_6)$alkyl$]_2$, $(C_2-C_6)$alkenyl, $(C_2-C_6)$alkynyl, $O-(C_1-C_6)$alkyl, $O-C(O)-(C_1-C_6)$alkyl, $PO_3H_2$, $SO_3H$, $SO_2-NH_2$, $SO_2NH(C_1-C_6)$alkyl, $SO_2N[(C_1-C_6)$alkyl$]_2$, $S-(C_1-C_6)$alkyl; $SO-(C_1-C_6)$alkyl, $SO_2-(C_1-C_6)$alkyl, $SO_2-N=CH-N[(C_1-C_6)$alkyl$]_2$, $C(NH)(NH_2)$, $NH_2$, $NH-(C_1-C_6)$alkyl, $N[(C_1-C_6)$alkyl$]_2$, $NH-C(O)-(C_1-C_6)$alkyl, $NH-C(O)O-(C_1-C_6)$alkyl, $NH-SO_2-(C_1-C_6)$alkyl, $NH-SO_2-(C_6-C_{10})$aryl, $NH-SO_2-(C_5-C_{10})$heterocyclyl, $N(C_1-C_6)$alkyl-$C(O)-(C_1-C_6)$alkyl, $N(C_1-C_6)$alkyl-$C(O)O-(C_1-C_6)$alkyl, $N(C_1-C_6)$alkyl-$C(O)-NH-(C_1-C_6)$alkyl], $(C_6-C_{10})$aryl, $(C_1-C_6)$alkylene-$(C_6-C_{10})$aryl, $O-(C_6-C_{10})$aryl, $O-(C_1-C_6)$alkylene-$(C_6-C_{10})$aryl, $(C_5-C_{10})$heterocyclyl, $(C_1-C_6)$alkylene-$(C_5-C_{10})$heterocyclyl, $O-(C_1-C_6)$alkylene-$(C_5-C_{10})$heterocyclyl, wherein the $(C_6-C_{10})$aryl or $(C_5-C_{10})$heterocyclyl may be substituted one to 3 times by a group independently selected from halogen, OH, $NO_2$, CN, $O-(C_1-C_6)$alkyl, $(C_1-C_6)$alkyl, $NH_2$, $NH(C_1-C_6)$alkyl, $N[(C_1-C_6)$alkyl$]_2$, $SO_2CH_3$, COOH, $C(O)O-(C_1-C_6)$alkyl, $CONH_2$, $(C_1-C_6)$alkylene-$O-(C_1-C_6)$alkyl, $(C_1-C_6)$alkylene-$O-(C_6-C_{10})$aryl, $O-(C_1-C_6)$alkylene-$(C_6-C_{10})$aryl; or wherein $(C_6-C_{10})$aryl is vicinally substituted by a $O-(C_1-C_4)$alkylene-O group whereby a 5-8-membered ring is formed together with the carbon atoms the oxygen atoms are attached to. Aryl or heterocyclyl substituents of $(C_6-C_{10})$aryl and $(C_5-C_{10})$heterocyclyl groups may not be further substituted by an aryl or heterocyclyl containing group.

Preferred substituents for $(C_6-C_{10})$aryl groups are $(C_1-C_4)$alkyl, $O-(C_1-C_4)$alkyl, O-phenyl, phenyl, $C(O)O-(C_1-C_6)$alkyl, C(O)OH, $C(O)-(C_1-C_4)$alkyl, halogen, $NO_2$, $SO_2NH_2$, CN, $SO_2-(C_1-C_4)$alkyl, $SO_2-N=CH-N[(C_1-C_6)$alkyl$]_2$, $NH-SO_2-(C_1-C_4)$alkyl, $NH_2$, $NH-C(O)-(C_1-C_4)$alkyl, $(C_3-C_8)$cycloalkyl, $(C_1-C_4)$alkyl-OH, $C(O)N[(C_1-C_4)$alkyl$]_2$, $C(O)NH(C_1-C_6)$alkyl, $C(O)NH_2$, $N[(C_1-C_4)$alkyl$]_2$, $(C_1-C_4)$alkylene-$(C_6-C_{10})$aryl, wherein the $(C_6-C_{10})$aryl may be further substituted one to three times, preferably once, by $(C_1-C_4)$alkyl, $(C_1-C_4)$alkylene-$O-(C_1-C_6)$alkyl, $(C_6-C_{10})$aryl $O-(C_1-C_6)$alkyl-$(C_6-C_{10})$aryl, or may be vicinally substituted by a $O-(C_1-C_4)$alkylene-O group whereby a 5-8-membered ring is formed together with the carbon atoms the oxygen atoms are attached to. More preferred substituents for $(C_6-C_{10})$aryl are halogen, CN, phenyl, O-phenyl, $NH-C(O)-(C_1-C_4)$alkyl especially $NH-C(O)-CH_3$, $C(O)-(C_1-C_4)$alkyl especially $C(O)-CH_3$, $C(O)-O(C_1-C_4)$alkyl especially $C(O)-OCH_3$, $(C_1-C_4)$alkyl especially $CH_3$ or $CF_3$, $O-(C_1-C_4)$alkyl especially $O-CH_3$, $SO_2-NH_2$, $SO_2-(C_1-C_4)$alkyl especially $SO_2-CH_3$ or $SO_2-CF_3$; or $SO_2-N=CH-N[(C_1-C_4)$alkyl$]_2$ especially $SO_2-N=CH-N[(CH_3)_2$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

Preferred substituents for $(C_5-C_{10})$heterocyclyl groups are $(C_1-C_4)$alkyl, O—$(C_1-C_4)$alkyl, $(C_1-C_4)$alkylene-phenyl, halogen, $(C_1-C_4)$alkylene-O—$(C_1-C_4)$alkyl, $(C_5-C_{10})$heterocyclyl, $(C_1-C_4)$alkylene-N[$(C_1-C_4)$alkyl]$_2$, or $(C_6-C_{10})$aryl, wherein the $(C_6-C_{10})$aryl may be further substituted by halogen, $(C_1-C_4)$alkyl, O—$(C_1-C_4)$alkyl, $(C_1-C_4)$alkylene-O—$(C_1-C_6)$alkyl, O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_5-C_{10})$heterocyclyl groups are $(C_1-C_4)$alkyl, O—$(C_1-C_4)$alkyl, halogen or phenyl, wherein the phenyl may be further substituted one to three times, preferably once, by halogen, $(C_1-C_4)$alkyl or O—$(C_1-C_4)$alkyl.

The general and preferred substituents of $(C_6-C_{10})$aryl and $(C_5-C_{10})$heterocyclyl groups may be combined with the general and preferred definitions of $R_1$, $R_2$, $R_3$, $R_4$, $R_5$, $R_6$, $R_6'$, $R_7$, $R_8$, n, m and L as described above.

Embodiments

In a further embodiment the compound of formula (I) is characterized by a compound of the formula (I')

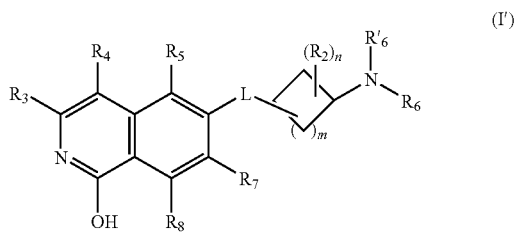

The compounds of formula (I) and (I') are tautomeric forms of each other and part of the present invention. The following embodiments refer to the compounds of formula (I) and (I').

$R_3$ is preferably H, halogen, $(C_1-C_4)$alkylene-R', O—R" or NHR". More preferred, $R_3$ is H or NHR". Most preferred, $R_3$ is H, NH—$(C_5-C_6)$heterocyclyl or NH-phenyl, especially preferred are H, NH—$(C_5-C_6)$heteroaryl containing one or more N atoms or NH-phenyl. Most especially preferred, $R_3$ is H.

Examples of $R_3$ substituents are

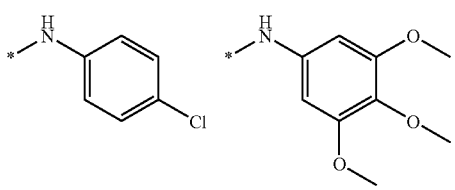

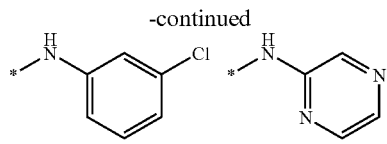

Preferably, $R_4$ is H, halogen or $(C_1-C_6)$alkyl. More preferred, $R_4$ is H, halogen or $(C_1-C_4)$alkyl. Most preferred, $R_4$ is H.

Preferably, $R_5$ is H, halogen, CN, $(C_1-C_6)$alkyl, $(C_2-C_6)$alkenyl, R', NH—$(C_6-C_{10})$aryl or $(C_1-C_6)$alkylene-R'. More preferably, $R_5$ is H, halogen, $(C_1-C_6)$alkyl, $(C_2-C_6)$alkenyl, R', NH—$(C_6-C_{10})$aryl or $(C_1-C_6)$alkylene-R'. Most preferably, $R_5$ is H, halogen, $(C_1-C_6)$alkyl, $(C_2-C_6)$alkenyl, $(C_6-C_{10})$aryl, NH—$(C_6-C_{10})$aryl, $(C_1-C_2)$alkyl-$(C_6-C_{10})$aryl or $(C_5-C_{10})$heteroaryl. Especially preferred, $R_5$ is H, halogen, phenyl, $(C_1-C_6)$alkyl, $(C_2-C_6)$alkenyl, $(C_6-C_{10})$aryl or $(C_5-C_6)$heteroaryl.

Most especially preferred $R_5$ is H, halogen, methyl, ethyl, vinyl, phenyl, thienyl or pyridyl.

Examples of $R_5$ are hydrogen, fluoro, chloro, bromo, iodo, methyl, ethyl, vinyl, phenyl, thienyl or pyridyl, nitrile, nitro, (p-methoxy)-phenyl, N-aniline, benzyl, 2-propenyl, s-butenyl, cyclopropyl, tetrazol, amino, 4-methoxy-aniline or N-acetyl, preferably hydrogen, fluoro, chloro, bromo, iodo, methyl, ethyl, vinyl, phenyl, thienyl or pyridyl. More preferred, $R_5$ is H, halogen, methyl, or ethyl, most preferred $R_5$ is H.

Preferably, $R_6$ and $R_6'$ are independently of each other H, $(C_1-C_6)$alkyl, R', $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_4)$alkylene-C(O)—$(C_5-C_{10})$heterocyclyl, $(C_1-C_4)$alkylene-C(O)—$(C_6-C_{10})$aryl, $(C_1-C_6)$alkylene-C(O)N[$(C_1-C_6)$alkyl]$_2$, $(C_1-C_6)$alkylene-C(O)NH—$(C_1-C_6)$alkyl, $(C_1-C_6)$alkylene-C(O)O—$(C_1-C_6)$alkyl, C(O)R'C(O)$(C_1-C_6)$alkyl, C(O)O—$(C_1-C_6)$alkyl, C(O)NH—$(C_1-C_6)$alkyl, C(O)N[$(C_1-C_6)$alkyl]$_2$, or C(O)$(C_1-C_6)$alkylene-R', or $R_6$ and $R_6'$, together with the N-atom to which they are attached, form a $(C_5-C_{10})$heterocyclyl group.

In a further preferred embodiment, $R_6$ and $R_6'$ are independently of each other H, $(C_1-C_6)$alkyl, $(C_5-C_{10})$heterocyclyl, $(C_3-C_8)$cycloalkyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)N[$(C_1-C_6)$alkyl]$_2$, $(C_1-C_6)$alkylene-C(O)NH—$(C_1-C_6)$alkyl, $(C_1-C_6)$alkylene-C(O)O—$(C_1-C_6)$alkyl, C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N[$(C_1-C_6)$alkyl]$_2$, C(O)$(C_1-C_6)$alkylene-$(C_3-C_8)$cycloalkyl, C(O)$(C_1-C_6)$alkylene-$(C_5-C_{10})$heterocyclyl, C(O)$(C_1-C_6)$alkylene-$(C_6-C_{10})$aryl, or $R_6$ and $R_6'$, together with the N-atom to which they are attached form a $(C_5-C_{10})$heterocyclyl group.

In a more preferred embodiment, $R_6$ is H, $(C_1-C_6)$alkyl, $(C_3-C_6)$cycloalkyl or $(C_1-C_4)$alkylene-$(C_3-C_6)$cycloalkyl, and $R_6'$ is H, $(C_1-C_6)$alkyl, $(C_3-C_8)$cycloalkyl, $(C_5-C_{10})$heterocyclyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)NH—$(C_1-C_6)$alkyl, $(C_1-C_6)$alkylene-C(O)N[$(C_1-C_6)$alkyl]$_2$, $(C_1-C_6)$alkylene-C(O)O—$(C_1-C_6)$alkyl, C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N[$(C_1-C_6)$ alkyl]$_2$, C(O)(C$_1$-C$_6$)alkylene-C$_3$-C$_8$)cycloalkyl, C(O)(C$_1$-C$_6$)alkylene-(C$_5$-C$_{10}$)heterocyclyl, C(O)(C$_1$-C$_6$)alkylene-(C$_6$-C$_{10}$)aryl, or R$_6$ and R$_6$', together with the N-atom to which they are attached, form a (C$_5$-C$_{10}$)heterocyclyl group.

In a further more preferred embodiment, R$_6$ is H, (C$_1$-C$_6$)alkyl and R$_6$' is H, (C$_1$-C$_6$)alkyl, (C$_3$-C$_8$)cycloalkyl, (C$_6$-C$_{10}$)aryl, (C$_5$-C$_{10}$)heterocyclyl, (C$_1$-C$_4$)alkylene-(C$_3$-C$_8$)cycloalkyl, (C$_1$-C$_4$)alkylene-(C$_5$-C$_{10}$)heterocyclyl, (C$_1$-C$_6$)alkylene-(C$_6$-C$_{10}$)aryl, (C$_1$-C$_4$)alkylene-O—(C$_1$-C$_4$)alkyl, (C$_1$-C$_4$)alkylene-C(O)N[(C$_1$-C$_4$)alkyl]$_2$, (C$_1$-C$_6$)alkylene-C(O)NH—(C$_1$-C$_6$)alkyl, C(O)(C$_1$-C$_6$)alkyl, C(O)(C$_1$-C$_6$)alkylene-(C$_5$-C$_{10}$)heterocyclyl, or R$_6$ and R$_6$', together with the N-atom to which they are attached, form a (C$_5$-C$_{10}$)heterocyclyl group.

In a further even more preferred embodiment, R$_6$ is H, (C$_1$-C$_6$)alkyl and R$_6$' is H;
(C$_1$-C$_6$)alkyl;
(C$_3$-C$_8$)cycloalkyl;
(C$_1$-C$_4$)alkylene-(C$_3$-C$_8$)cycloalkyl;
(C$_1$-C$_4$)alkylene-O—(C$_1$-C$_4$)alkyl;
(C$_1$-C$_4$)alkylene-C(O)N [(C$_1$-C$_4$)alkyl]$_2$;
(C$_1$-C$_4$)alkylene-(C$_5$-C$_{10}$)heterocyclyl wherein heterocyclyl is unsubstituted or substituted one or more times, preferably one to three times, more preferably one or two times, by a group independently selected from (C$_1$-C$_4$)alkyl, O—(C$_1$-C$_4$)alkyl, halogen or phenyl, or is substituted once by (C$_5$-C$_6$)heterocyclyl,
wherein phenyl or (C$_5$-C$_6$)heterocyclyl are unsubstituted or substituted one to three times by halogen, (C$_1$-C$_4$)alkyl or O—(C$_1$-C$_4$)alkyl; or
(C$_1$-C$_4$)alkylene-(C$_6$-C$_{10}$)aryl wherein aryl is unsubstituted or substituted one or more times, preferably one to three times, by a group independently selected from halogen, (C$_1$-C$_4$)alkyl preferably CH$_3$ or CF$_3$, O—(C$_1$-C$_4$)alkyl, CN, SO$_2$—NH$_2$; SO$_2$—(C$_1$-C$_4$)alkyl preferably SO$_2$—CH$_3$ or SO$_2$—CF$_3$; SO$_2$—N=CH—N[(C$_1$-C$_4$)alkyl]$_2$, preferably SO$_2$—N=N—N(CH$_3$)$_2$, NH—CO—(C$_1$-C$_4$)alkyl preferably NH—CO—CH$_3$, or CO—O—(C$_1$-C$_4$)alkyl, and (C$_6$-C$_{10}$)aryl is substituted once by unsubstituted phenyl, unsubstituted O-phenyl or unsubstituted (C$_5$-C$_6$)heterocyclyl;
C(O)(C$_1$-C$_4$)alkyl;
C(O)(C$_1$-C$_4$)alkylene-(C$_5$-C$_{10}$)heterocyclyl;
or R$_6$ and R$_6$', together with the N-atom to which they are attached, form a (C$_5$-C$_6$)heterocyclyl group, which is unsubstituted or substituted one to three times, preferably once, by (C$_1$-C$_4$)alkyl or C(O)O(C$_1$-C$_4$)alkyl;
wherein a (C$_1$-C$_4$)alkyl or (C$_1$-C$_6$)alkyl residue is unsubstituted or substituted one to three times by halogen, preferably by fluoro.

Preferably the formed heterocyclyl group is morpholino, piperidino, pyrrolidino or piperazino, which can be unsubstituted or substituted as described above. More preferably the heterocyclyl group is morpholino or 4-ethyl-piperazinyl.

In a most preferred embodiment, R$_6$ is H, (C$_1$-C$_6$)alkyl and R$_6$' is H, (C$_1$-C$_6$)alkyl, (C$_3$-C$_8$)cycloalkyl, In a further most preferred embodiment, R$_6$ is H and R$_6$' is H, preferably unsubstituted (C$_1$-C$_6$)alkyl, or preferably unsubstituted (C$_3$-C$_8$)cycloalkyl. Especially preferred, R$_6$ and R$_6$' are H.

In one embodiment R6 is not tertbutyloxycarbonyl, especially if m is 3.

As examples for these embodiments, R$_6$ or R$_6$' are, independently from each other, hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of

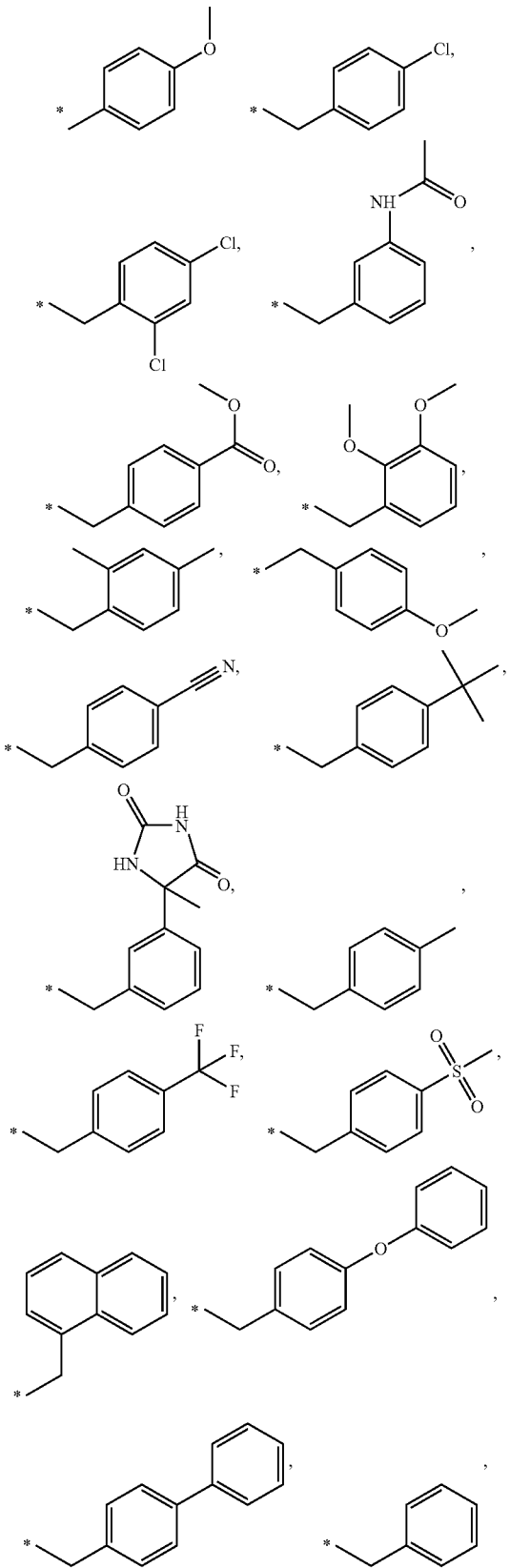

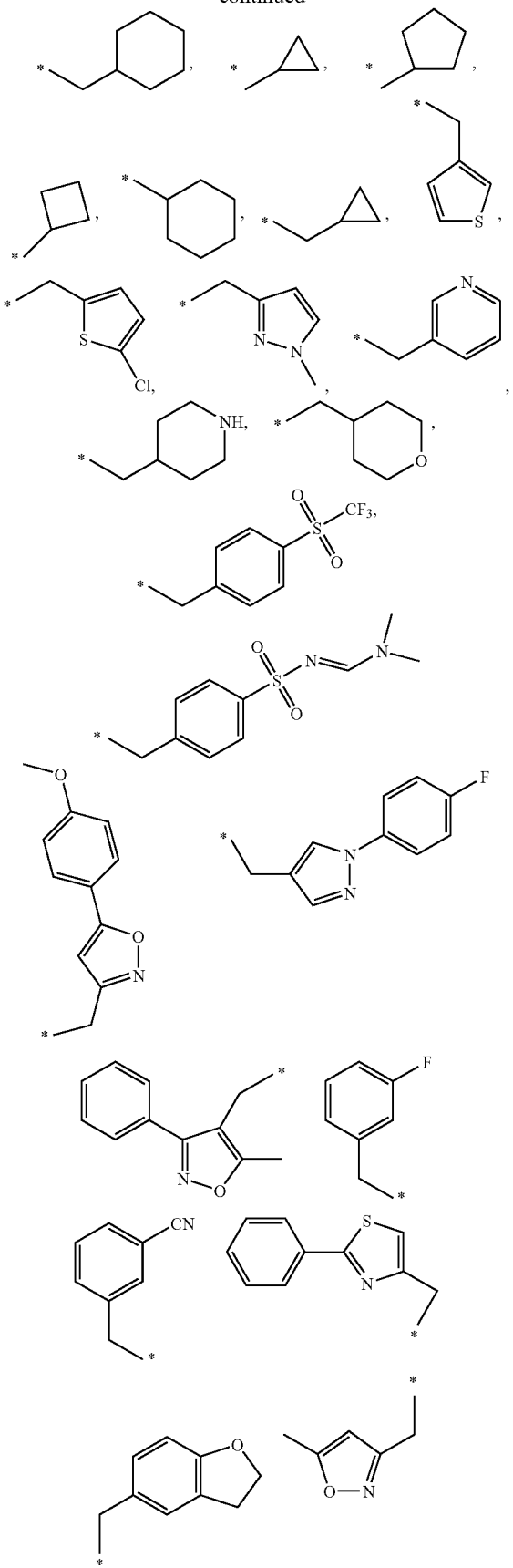
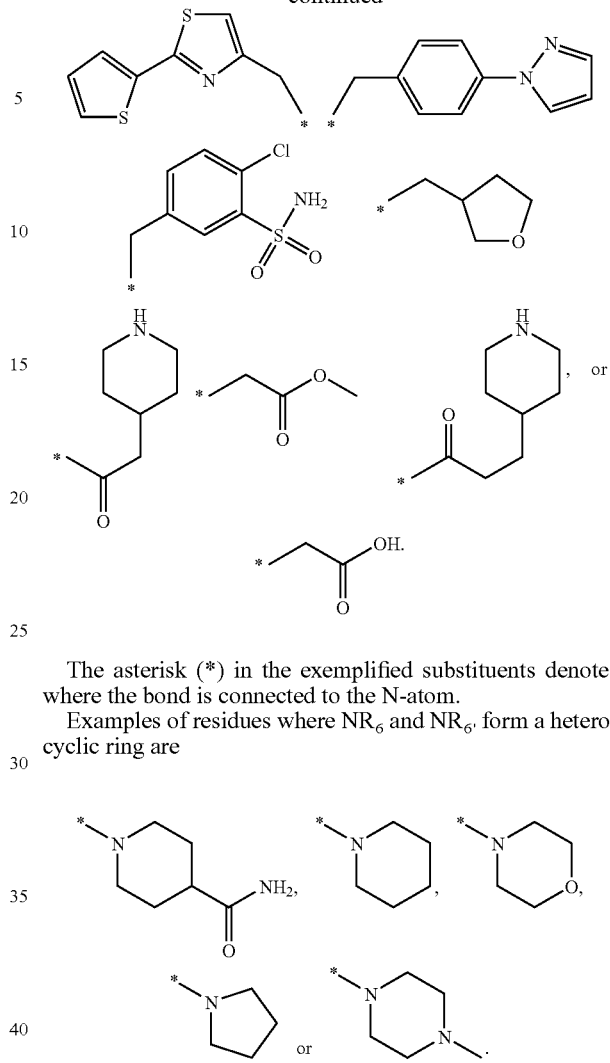

The asterisk (*) in the exemplified substituents denotes where the bond is connected to the N-atom.

Examples of residues where $NR_6$ and $NR_{6'}$ form a heterocyclic ring are

The asterisk (*) in the exemplified substituents denotes where the bond is connected to the carbon atom of the carbocycle.

Preferably, $R_7$ is H, halogen, CN, $(C_1-C_6)$alkyl, O—$(C_1-C_6)$alkyl, $(C_2-C_6)$alkenyl, R' or $(C_1-C_6)$alkylene-$(C_3-C_8)$cycloalkyl. More preferred, $R_7$ is H, halogen, CN, $(C_1-C_4)$alkyl, O—$(C_1-C_4)$alkyl, $(C_2-C_4)$alkenyl, phenyl, cyclopropyl or $(C_5-C_6)$heteroaryl. Most preferably, $R_7$ is H, fluoro, chloro, bromo, methyl, ethyl, methoxy, phenyl, nitrile, cyclopropyl, thienyl or vinyl, most especially preferred $R_7$ is H, fluoro, chloro, methyl or methoxy. More particular preferred $R_7$ is H.

$R_8$ is preferably H, halogen or $(C_1-C_4)$alkyl. More preferred, $R_8$ is H, Cl, F, methyl or ethyl. Most preferred $R_8$ is H.

Preferably, $R_2$ is H, halogen or $(C_1-C_4)$alkyl. Preferably, $R_2$ is H or $(C_1-C_2)$alkyl. More preferred, $R_2$ is H, methyl or ethyl. Most preferred $R_2$ is H. $R_2$ may be bound to any carbon atom of the ring including the position where the linker group L is bound.

Preferably, n is 1, 2 or 3. More preferred, n is 1 or 2. Most preferred n is 1.

Preferably m is 2, 3 or 4. More preferred m is 3. In a further embodiment m is 1, 2, 4 or 5.

The linker group L may be bound to the ring in any position via a ring carbon atom. In a preferred embodiment, m is 3 and L is attached to the 4-position of the amino cyclohexane ring

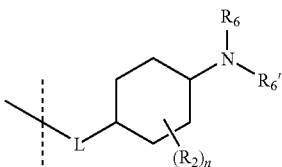

or L is attached to the 3-position of the amino cyclohexane ring

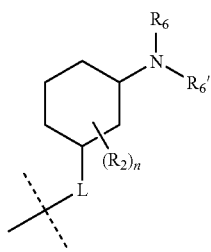

in all their sterechemical forms.

In an especially preferred embodiment, L is attached to the 4-position of the amino cyclohexane ring.

In a further preferred embodiment, L is O-methylene, O-ethylene or preferably O. More preferably, m is 3 and L is O-methylene, O-ethylene or O attached to the 4-position of the amino cyclohexane ring.

In residues $R_2$ to $R_8$ an alkyl or alkylene can optionally be substituted one or more times by halogen. Preferably alkyl or alkylene is substituted one to three times by halogen selected from chloro or bromo but may be substituted by fluoro once or more, e.g. being perfluorinated. Preferably halogen is fluor. More preferred an alkyl or alkylene is not halogenated.

In residues $R_4$, $R_5$, $R_6$, $R_6'$, $R_7$ and $R_8$ alkyl, alkylene or cycloalkyl can optionally be substituted one or more times by a group selected independently from OH, $OCH_3$, COOH, $COOCH_3$, $NH_2$, $NHCH_3$, $N(CH_3)_2$, $CONHCH_3$ or $CON(CH_3)_2$.

If substituted, the number of substituents is preferably between 1, 2, 3 or 4, more preferably 1 or 2 with 1 being even more preferred. Preferably an alkylene or cycloalkyl is not substituted. More preferably an alkyl, alkylene or cycloalkyl is not substituted. Preferably alkyl, alkylene or cycloalkyl in $R_4$, $R_5$, $R_7$ and $R_8$ are not substituted. In a further embodiment alkyl, alkylene or cycloalkyl in $R_4$, $R_5$, $R_6$, $R_7$ and $R_8$ are not substituted.

In preferred embodiments of the present invention one or more or all of the groups contained in the compounds of formula (I) or (I') can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) or (I') in all stereoisomeric forms and mixtures of stereoisomeric forms in all ratios, and their pharmaceutically acceptable salts.

The term "*-" in the exemplified substituents vide supra marks the point where the substituent is attached, which means, for example, for a $R_3$ substituent

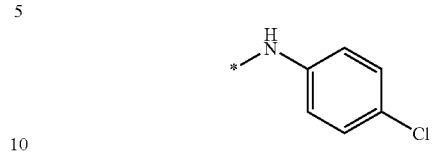

and m is 3 a compound of the formula

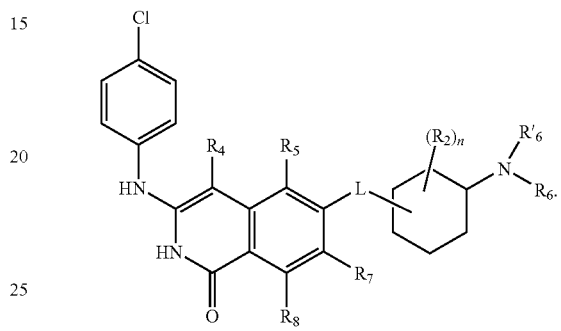

A preferred embodiment is a compound of the formula (I) wherein
$R_2$ is hydrogen, halogen, or $(C_1-C_6)$alkyl;
$R_3$ is H, halogen, $(C_1-C_4)$alkylene-R', O—R" or NHR";
$R_4$ is H, halogen or $(C_1-C_6)$alkyl;
$R_5$ is H, $(C_1-C_6)$alkyl, halogen, CN, $(C_2-C_6)$alkenyl, $(C_6-C_{10})$aryl, NH—$(C_6-C_{10})$aryl, $(C_1-C_6)$alkylene-$(C_6-C_{10})$aryl, $(C_5-C_{10})$heterocyclyl or
$(C_1-C_6)$alkylene-$(C_5-C_{10})$heterocyclyl;
$R_6$ and $R_6'$ are independently of each other H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)$NH_2$, $(C_1-C_6)$alkylene-C(O)NH—R', $(C_1-C_6)$alkylene-C(O)N [$(C_1-C_4)$alkyl]$_2$, $(C_1-C_6)$alkylene-C(O)N[R']$_2$, C(O)O—$(C_1-C_6)$alkyl, C(O)$(C_1-C_6)$alkyl, C(O)$(C_3-C_8)$cycloalkyl, C(O)$(C_5-C_{10})$heterocyclyl, C(O)NH—$(C_1-C_6)$alkyl, C(O)N [$(C_1-C_6)$alkyl]$_2$, C(O)—$(C_1-C_6)$alkylene-$(C_3-C_8)$cycloalkyl, C(O)$(C_1-C_6)$alkylene-$(C_5-C_{10})$heterocyclyl, C(O)$(C_1-C_6)$alkylene-$(C_6-C_{10})$aryl, or $R_6$ and $R_6'$, together with the N-atom to which they are attached, form a $(C_5-C_6)$heterocyclyl group.
$R_7$ is H, halogen, CN, $(C_1-C_6)$alkyl, O—$(C_1-C_6)$alkyl, $(C_2-C_6)$alkenyl or R';
$R_8$ is H, halogen or $(C_1-C_6)$alkyl;
m is 2, 3 or 4
n is 1, 2 or 3, and
L is O,O-methylene or O-ethylene;
and their pharmaceutically acceptable salts.

A further preferred embodiment is a compound of the formula (I) wherein
$R_2$ is H or $(C_1-C_4)$alkyl;
$R_3$ is H, halogen or NHR";
$R_4$ is H, halogen or $(C_1-C_4)$alkyl;
$R_5$ is H, $(C_1-C_6)$alkyl, halogen, $(C_2-C_4)$alkenyl, $(C_6-C_{10})$aryl, $(C_1-C_6)$alkylene-$(C_6-C_{10})$aryl or $(C_5-C_{10})$heterocyclyl;
$R_6$ and $R_6'$ are independently of each other H, $(C_3-C_8)$cycloalkyl, $(C_1-C_8)$alkyl, $(C_1-C_6)$alkylene-O—$(C_1-C_6)$alkyl, $(C_1-C_3)$alkylene-R', C(O)$(C_1-C_6)$alkyl, C(O)$(C_3-C_8)$cycloalkyl, C(O)$(C_5-C_{10})$heterocyclyl, C(O)$(C_1-C_6)$alkylene-$C_3$-$C_8$)cycloalkyl, C(O)($C_1$-$C_6$)alkylene-($C_5$-$C_{10}$)heterocyclyl or C(O)($C_1$-$C_6$)alkylene-($C_6$-$C_{10}$)aryl;

$R_7$ is H, halogen, CN, ($C_1$-$C_6$)alkyl, O—($C_1$-$C_6$)alkyl, ($C_2$-$C_6$)alkenyl or R';

$R_8$ is H, halogen or ($C_1$-$C_6$)alkyl;

m is 2, 3 or 4 n is 1, 2 or 3; and

L is O;

and their pharmaceutically acceptable salts.

An especially preferred embodiment is a compound of the formula (I) wherein $R_2$ is H, ($C_1$-$C_4$)alkyl;

$R_3$ is H, NH—($C_5$-$C_6$)heteroaryl or NH-phenyl;

$R_4$ is H, halogen or ($C_1$-$C_4$)alkyl;

$R_5$ is H, ($C_1$-$C_4$)alkyl, halogen, ($C_2$-$C_4$)alkenyl, ($C_6$-$C_{10}$)aryl, ($C_1$-$C_2$)alkyl-($C_6$-$C_{10}$)aryl or ($C_5$-$C_6$)heteroaryl;

$R_6$ is H, ($C_3$-$C_6$)cycloalkyl or ($C_1$-$C_4$)alkyl;

$R_6$' is H, ($C_3$-$C_8$)cycloalkyl, ($C_1$-$C_8$)alkyl, ($C_1$-$C_3$)alkylene-R', C(O)O—($C_1$-$C_6$)alkyl, C(O)($C_1$-$C_6$)alkyl, C(O)($C_3$-$C_6$)cycloalkyl, C(O)($C_5$-$C_6$)heterocyclyl, C(O)($C_1$-$C_3$)alkylene-($C_3$-$C_6$)cycloalkyl, C(O)($C_1$-$C_3$)alkylene-($C_5$-$C_6$)heterocyclyl, or C(O)($C_1$-$C_3$)alkylene-phenyl;

$R_7$ is H, halogen, CN, ($C_1$-$C_4$)alkyl, O—($C_1$-$C_4$)alkyl, ($C_2$-$C_4$)alkenyl, phenyl, cyclopropyl, ($C_5$-$C_6$)heteroaryl;

$R_8$ is H, halogen or ($C_1$-$C_4$)alkyl;

m is 3 n is 1; and

L is O; or a pharmaceutically acceptable salt thereof.

In an embodiment the present invention relates to a compound of formula (I) or formula (I') independently selected from the group of 15 1-[4-(7-Chloro-1-oxo-1,2-dihydro-isoquinolin-6-yloxy)-cyclohexyl]-piperidine-4-carboxylic acid amide, 16 7-Chloro-6-(4-piperidin-1-yl-cyclohexyloxy)-2H-isoquinolin-1-one, 17 7-Chloro-6-(4-morpholin-4-yl-cyclohexyloxy)-2H-isoquinolin-1-one, 19 7-Chloro-6-(4-pyrrolidin-1-yl-cyclohexyloxy)-2H-isoquinolin-1-one, 21 7-Chloro-6-[4-(4-methyl-piperazin-1-yl)-cyclohexyloxy]-2H-isoquinolin-1-one, 23 [4-(7-Chloro-1-oxo-1,2-dihydro-isoquinolin-6-yloxy)-cis-cyclohexylamino]-acetic acid ethyl ester, 24 [4-(7-Chloro-1-oxo-1,2-dihydro-isoquinolin-6-yloxy)-cis-cyclohexylamino]-acetic acid, 27 7-Methyl-6-(4-pyrrolidin-1-yl-cyclohexyloxy)-2H-isoquinolin-1-one, 28 N-[4-(7-Methyl-1-oxo-1,2-dihydro-isoquinolin-6-yloxy)-trans-cyclohexyl]-3-piperidin-4-yl-propionamide, 29 N-[4-(7-Methyl-1-oxo-1,2-dihydro-isoquinolin-6-yloxy)-trans-cyclohexyl]-2-piperidin-4-yl-acetamide, 30 N-[4-(7-Chloro-1-oxo-1,2-dihydro-isoquinolin-6-yloxy)-cis-cyclohexyl]-3-piperidin-4-yl-propionamide, 31 N-[4-(7-Chloro-1-oxo-1,2-dihydro-isoquinolin-6-yloxy)-cis-cyclohexyl]-2-piperidin-4-yl-acetamide, 43 6-((1S,3S)-3-Amino-cyclopentyloxy)-2H-isoquinolin-1-one, 44 6-((1S,3S)-3-Amino-cyclopentyloxy)-7-chloro-2H-isoquinolin-1-one, 45 6-((1S,3R)-3-Amino-cyclopentyloxy)-2H-isoquinolin-1-one, 46 6-((1S,3R)-3-Amino-cyclopentyloxy)-7-chloro-2H-isoquinolin-1-one, 47 6-((cis-4-Amino-cycloheptyloxy)-7-methyl-2H-isoquinolin-1-one, or 48 7-Chloro-6-(cis-4-Amino-cycloheptyloxy)-2H-isoquinolin-1-one, or their stereoisomeric forms and/or their pharmaceutically acceptable salts.

In another embodiment the present invention relates to a compound of formula (I) or (I') independently selected from the group of 49 6-(cis-4-Amino-cycloheptyloxy)-2H-isoquinolin-1-one, 54 6-(3-Amino-cyclobutoxy)-7-chloro-2H-isoquinolin-1-one, 55 cis-6-(3-Amino-cyclobutylmethoxy)-7-chloro-2H-isoquinolin-1-one, 56 trans-6-(3-Amino-cyclobutylmethoxy)-7-chloro-2H-isoquinolin-1-one, 62 6-(5-Amino-cyclooctyloxy)-7-chloro-2H-isoquinolin-1-one, 65 5-(1-Benzyloxy-7-chloro-isoquinolin-6-yloxy)-1-propyl-cyclooctylamine, 66 6-(5-Amino-5-propyl-cyclooctyloxy)-7-chloro-2H-isoquinolin-1-one, 68 6-(5-Benzyl-amino-5-propyl-cyclo-octyloxy)-7-chloro-2H-isoquinolin-1-one, 69 7-Chloro-6-(5-ethylamino-5-propyl-cyclooctyloxy)-2H-isoquinolin-1-one, 70 7-Chloro-6-(cis-3-isopropylamino-cyclobutoxy)-2H-isoquinolin-1-one, 71 6-(3-cis-Benzylamino-cyclobutoxy)-7-chloro-2H-isoquinolin-1-one, 72 6-(3-trans-Benzylamino-cyclobutoxy)-7-chloro-2H-isoquinolin-1-one, 73 7-Chloro-6-(3-cis-dibenzylamino-cyclobutoxy)-2H-isoquinolin-1-one, 74 7-Chloro-6-(3-trans-dibenzylamino-cyclobutoxy)-2H-isoquinolin-1-one or 75 7-Chloro-6-(3-trans-diethylamino-cyclobutoxy)-2H-isoquinolin-1-one, or their stereoisomeric forms and/or their pharmaceutically acceptable salts. (Compound Number Given for Reference)

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Isoquinoline substitution pattern is numbered according to IUPAC rules:

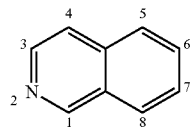

All references to "compound(s) of formula (I) or (I')" hereinafter refer to compound(s) of the formula (I) or (I') as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) or (I') mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) or (I') which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) or (I') have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula (I) or (I') of the invention, for example an N-oxide, which on administration to a mammal such as, for example, a human is able to form (directly or indirectly) a compound of the formula (I) or (I') or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I) or (I') in the form of their stereoisomeric forms, which include racemates, racemic mixtures, pure enantiomers and diastereomers and mixtures thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I) or (I'), they may all, independently of one another, have the stated meaning and be identical or different.

The present invention therefore also relates to the compounds of the formula (I) or (I') and/or their pharmaceutically acceptable salts and/or their prodrugs for use as pharmaceuticals (or medicaments), to the use of the compounds of the formula (I) or (I') and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The present invention furthermore relates to pharmaceutical preparations (or pharmaceutical compositions) which contain an effective amount of at least one compound of the formula (I) or (I') and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) or (I') and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) or (I') and/or their pharmaceutically acceptable salts and/or their prodrugs. The amount of the active ingredient of the formula (I) or (I') and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) or (I') and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) or (I') and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) or (I') allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) or (I') the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations.

As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formulae (I) or (I') can then be carried out by known processes.

In general, a reaction mixture containing a final compound of the formula (I) or (I') or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

Isoquinolinones can by synthesized via a variety of methods. The following general schemes illustrate some of the possible ways to access isoquinolones, but do not limit the present invention.

Scheme 1:

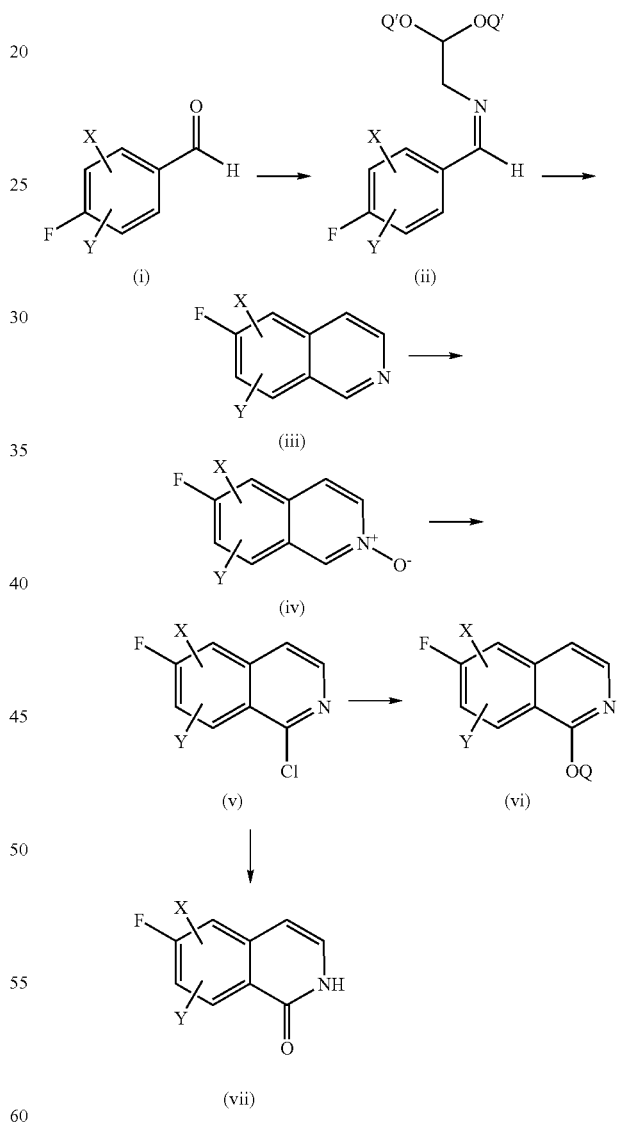

A suitably substituted aldehyde, for example substituted by X or Y being independently from each other hydrogen, alkyl, alkoxy or halide attached in a suitable position, can be reacted with a suitable compound such as for example an actual of aminoacetaldehyde for example in a solvent like THF, chloroform or toluene under acid catalysis by toluene sulfonic acid or another appropriate acid to give imine (ii) wherein Q' can be for instance methyl or ethyl, which in turn can be cyclized by different methods to the isoquinoline (iii). For example this can be done by Lewis acid catalysis by suitable Lewis acids like titanium tetrachloride, ferrous halides, aluminium halides etc. at temperatures ranging from ambient to 100° C. or by reducing the imine to the corresponding amine by action of a suitable reducing agent like sodium borohydride, converting the amine into an amide or sulphonamide by reaction with a suitable acid chloride and subsequent cyclization to the isoquinoline by action of an appropriate lewis acid. The isoquinoline (iii) itself can then be converted to the corresponding N-oxide (iv) by action of a suitable oxidative agent like hydrogen peroxide, m-chloro perbenzoic acid or others at room temperature or elevated temperature. The N-oxide (iv) can then be converted into the 1-chloro-isoquinoline derivative (v) by reacting it with a reagent like phosphorous oxy chloride in or without presence of phosphorous pentachloride. The derivative (v) can then be turned into suitable 1-alkoxy-derivatives by reacting it with various alcohols Q-OH like methanol, ethanol or benzyl alcohol in the presence of a suitable base like sodium hydride and in a suitable solvent like dimethyl formamide, dimethyl acetamide or others. Alternatively (v) can be directly converted into the isoquinolinone derivative (vii) by reacting it with a reagent like ammonium acetate.

Scheme 2:

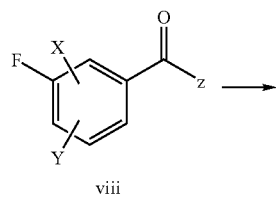

viii

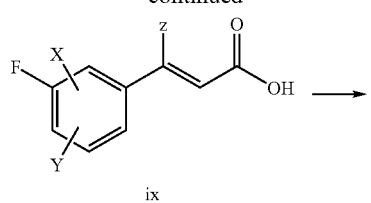

ix

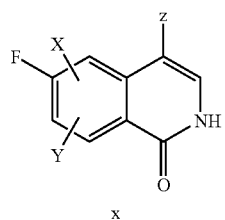

x

Alternatively isoquinolinones can be obtained by reacting suitable 3-formylated or acylated fluorobenzenes (viii), wherein z is for example H or alkyl like methyl or ethyl, with a reagent like triethyl phosphono acetate in the presence of a suitable base like sodium hydride to give the corresponding cinnamic acid ester, which subsequently is cleaved by action of a suitable base like potassium hydroxide, sodium hydroxide or lithium hydroxide in a suitable solvent to deliver acid (ix). (ix) can then be converted to the corresponding acid chloride by well known methods, which can be transferred into the acid azide by reaction with sodium azide in a suitable solvent like ether, chloroform or acetone in or without the presence of water. The corresponding azide then can be converted into isoquinolinone (x) by reacting it in a suitable solvent like diphenylmethane or diphenylether at suitable temperature.

Scheme 3:

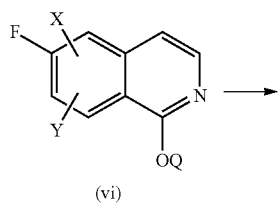

(vi)

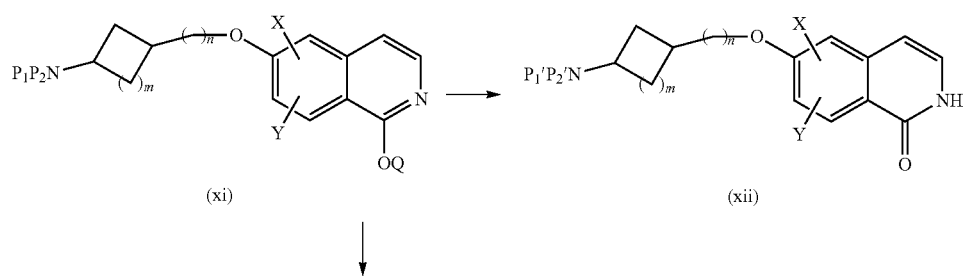

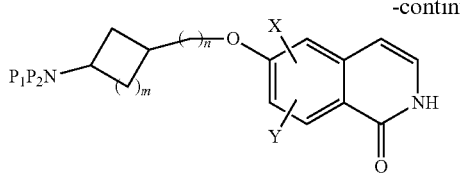

(xiii)

The above obtained 6-fluoro-isoquinolones, for example (vi), can be reacted with suitable $P_1/P_2$ substituted amino alcohols wherein $P_1/P_2$ are independently from each other for example hydrogen, alkyl or a protecting group like for example Boc or phthaloyl in the presence of base such as DBU, cesium carbonate or sodium hydride to give the corresponding alkoxy substituted derivatives (xi). Eventually, this conversion can already be performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base.

The products like (xi) obtained via this method can then either be liberated or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step like for example acidic removal of Boc-groups. Furthermore an amino group can be acylated by reacting it with a suitable acid chloride in the precence of a base like triethyl amine or Hünig's base or by reacting it with a suitable carboxylic acid in the precence of a base like triethylamine ot Hünig's base and a coupling reagent like EDC, PyBOP or TOTU.

In case of use of protected isoquinolones, cleavage of the used protection groups is required to liberate the desired isoquinolone (xii). This liberation, however, can be performed before or after the reductive amination step, depending on the nature of the used aldehyde/ketone and the protection group used.

Isoquinolone derivatives like (xii) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The general methods for the preparation of isoquinolinone derivatives as described above can be readily adapted to the preparation of the compounds of the formula (I) or (I'). In the following examples the preparation of the compounds of the present invention is outlined in more detail.

Accordingly, the following examples are part of and intended to illustrate but not to limit the present invention.

It is understood that modifications that do not substantially affect the activity of the various embodiments of this invention are included within the invention disclosed herein.

LC/MS-Methods:

| | Method A: |
|---|---|
| Stationary phase: | Col YMC Jsphere 33 × 2 |
| Gradient: | ACN + 0.05% TFA:$H_2O$ + 0.05% TFA |
| | 5:95(0 min) to 95:5(3.4 min) to 95:5(4.4 min) |
| Flow | 1 mL/min |
| | Method B: |
| Stationary phase: | Col YMC Jsphere 33 × 2 |
| Gradient: | ACN + 0.05% TFA:$H_2O$ + 0.05% TFA |
| | 5:95(0 min) to 95:5(2.5 min) to 95:5(3.0 min) |
| Flow | 1 mL/min |
| | Method C: |
| Stationary phase: | Col YMC Jsphere ODS H80 20 × 2 |
| Gradient: | ACN:$H_2O$ + 0.05% TFA |
| | 4:96(0 min) to 95:5(2.0 min) to 95:5(2.4 min) |
| Flow | 1 mL/min |
| | Method D: |
| Stationary phase: | Col YMC Jsphere 33 × 2.1 |
| Gradient: | ACN + 0.08% FA:$H_2O$ + 0.1% FA (Formic Acid) |
| | 5:95(0 min) to 95:5(2.5 min) to 95:5(3 min) |
| Flow | 1.3 mL/min |
| | Method E: |
| Stationary phase: | Col YMC Jsphere 33 × 2 |
| Gradient: | ACN + 0.05% TFA:$H_2O$ + 0.05% TFA |
| | 5:95(0 min) to 95:5(2.5 min) to 95:5(3.2 min) |
| Flow | 1.3 mL/min |
| | Method F: |
| Stationary phase: | Col YMC-Pack Pro C18 RS 33 × 2.1 |
| Gradient: | ACN + 0.1% FA:$H_2O$ + 0.1% FA (Formic Acid) |
| | 5:95(0 min) to 95:5(2.5 min) to 95:5(3 min) |
| Flow | 1.3 mL/min |
| | Method G: |
| Stationary phase: | Col YMC Jsphere 33 × 2.1 |
| Gradient: | ACN + 0.05% TFA:$H_2O$ + 0.05% TFA |
| | 2:98(0 min) to 2:98(1 min) to 95:5(5 min) |
| | to 95:5(6.25 min) |
| Flow | 1 mL/min |
| | Method H: |
| Stationary phase: | Col YMC Jsphere ODS H80 20 × 2 |
| Gradient: | ACN:$H_2O$ + 0.05% TFA |
| | 7:93(0 min) to 95:5(1.2 min) to 95:5(1.4 min) |
| Flow | 1.1 mL/min |
| | Method I: |
| Stationary phase: | Waters XBridge C18 4 |
| Gradient: | ACN + 0.05% TFA:$H_2O$ + 0.05% TFA |
| | 5:95(0 min) to 5:95(0.3 min) to 95:5(3.5 min) |
| | to 95:5 (4 min) |
| Flow | 1.3 mL/min |
| | Method J: |
| Stationary phase: | Col YMC Jsphere 33 × 2 |
| Gradient: | ACN + 0.05% TFA:$H_2O$ + 0.05% TFA |
| | 5:95(0 min) to 5:95(0.5 min) to 95:5(3.5 min) |
| | to 95:5 (4 min) |
| Flow | 1.3 mL/min |

(2,2-Dimethoxy-ethyl)-(4-fluoro-benzyl)-amine (1)

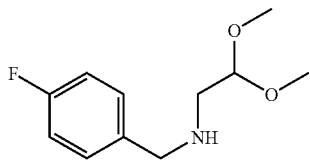

12.4 g of 4-fluorobenzaldehyde were dissolved in 100 mL of toluene and reacted with 10.5 g of 2-aminoacetaldehyde dimethylacetal and 1.90 g of p-toluenesulfonic acid monohydrate for two hours at a Dean Stark apparatus. The solution was allowed to cool down, extracted with saturated sodium bicarbonate solution, water and brine, dried over magnesium sulfate and evaporated to dryness. The crude product was dissolved in 100 mL of ethanol. 1.89 g of sodium borohydride were added portionwise. Stirring was continued overnight. For workup, acetic acid was added until no gas evolution could be observed. Then the solution was evaporated to dryness, taken up in dichloromethane and washed twice with water. The organic layer was extracted with brine, dried over magnesium sulfate and evaporated to dryness. The obtained crude product (20 g) was used for further reactions without purification. $R_t$=0.86 min (Method B). Detected mass: 182.1 (M-OMe$^-$), 214.2 (M+H$^+$).

N-(2,2-Dimethoxy-ethyl)-N-(4-fluoro-benzyl)-4-methyl-benzene-sulfonamide (2)

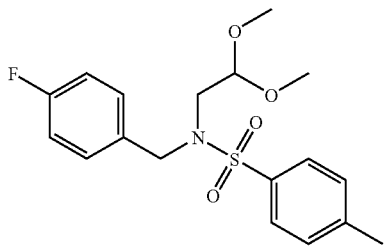 [SMILES: COC(CN(Cc1ccc(F)cc1)S(=O)(=O)c1ccc(C)cc1)OC]

20 g of (2,2-dimethoxy-ethyl)-(4-fluoro-benzyl)-amine (1) were dissolved in 120 ml of dichloromethane. 20 mL of pyridine were added. At 0° C. a solution of 23.8 g p-toluenesulfonic acid chloride in dichloromethane was added dropwise. The reaction was allowed to warm to room temperature and stirring was continued until conversion was completed. For workup, the reaction mixture was washed twice with 2M hydrochloric acid, twice with sodium bicarbonate solution and once with brine. The organic layer was dried over magnesium sulfate, evaporated to dryness and the obtained crude product was purified by silica gel chromatography to yield 22.95 g of compound 2 as an orange oil. $R_t$=1.71 min (Method C). Detected mass: 336.1 (M-OMe$^-$).

6-Fluoro-isoquinoline (3)

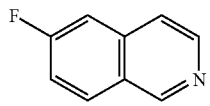

41.6 g of AlCl$_3$ were suspended in 400 mL of dichloromethane. At room temperature, a solution of 22.95 g N-(2,2-dimethoxy-ethyl)-N-(4-fluoro-benzyl)-4-methyl-benzene-sulfonamide (2) in 150 ml of dichloromethane was added. Stirring was continued at room temperature overnight, the solution was poured on ice, the layers were separated, the aqueous phase was extracted twice with dichloromethane and the combined organic layers were then extracted twice with sodium bicarbonate solution. The organic layer was dried over magnesium sulfate, evaporated to dryness and the obtained crude product (8.75 g) was purified by silica gel chromatography to yield 2.74 g of compound 3. $R_t$=0.30 min (Method C). Detected mass: 148.1 (M+H$^+$).

7-Chloro-6-fluoro-isoquinoline (4)

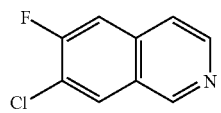 [SMILES: Fc1cc2ccncc2cc1Cl]

Starting from 3-chloro-4-fluoro-benzaldehyde, the title compound was prepared by the same reaction sequence as used for the synthesis of 6-fluoro-isoquinoline (3). $R_t$=0.77 min (Method A). Detected mass: 182.1/184.1 (M+H$^+$).

7-Chloro-6-fluoro-isoquinoline 2-oxide (5)

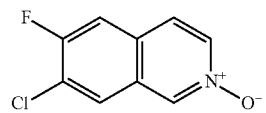 [SMILES: [O-][n+]1ccc2cc(F)c(Cl)cc2c1]

25 g (137.7 mmol) of 7-chloro-6-fluoro-isoquinoline (4) were dissolved in 500 ml of dichloromethane. At room temperature, 50.9 g (206.5 mmol) of m-chloro perbenzoic acid (70%) were added and the mixture was stirred at room temperature until complete conversion is achieved. For workup, the precipitate was filtered off and washed with dichloromethane. The filtrate was washed twice with sodium bicarbonate solution. The layers were separated and the aqueous phase was extracted twice with dichloromethane. The organic phases were dried with magnesium sulfate and evaporated. The so obtained solid material (18.4 g) was used without further purification. $R_t$=0.87 min (Method C). Detected mass: 198.1/200.1 (M+H$^+$).

1,7-Dichloro-6-fluoro-isoquinoline (6)

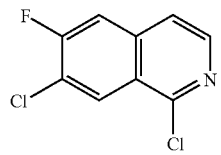 [SMILES: Fc1cc2ccnc(Cl)c2cc1Cl]

2.6 g (12.0 mmol) of 7-chloro-6-fluoro-isoquinoline 2-oxide (5) were heated in 40 ml of POCl$_3$ at reflux for 4 h. After the mixture had cooled down to room temperature, it was poured on ice. The aqueous solution was extracted three times with dichloromethane. The combined organic layers were dried with magnesium sulfate and evaporated to yield 2.91 g of the title compound, which was used without further purification. $R_t$=2.34 min (Method A). Detected mass: 216.0/218.0 (M+H$^+$).

7-Chloro-6-fluoro-2H-isoquinolin-1-one (7)

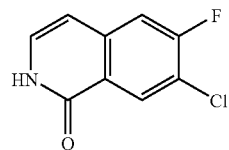 [SMILES: O=c1[nH]ccc2cc(F)c(Cl)cc12]

41.13 g (190.4 mmol) 1,7-dichloro-6-fluoro-isoquinoline (6) were dissolved in 670 ml of acetic acid. After addition of 148.8 g (1.90 mol) of ammonium acetate, the solution was stirred at 100° C. After 3 h, the solvent was removed under reduced pressure and the residue was poured into water. The aqueous phase was extracted three times with dichloromethane, the combined organic layer was washed with saturated sodium bicarbonate solution and brine, dried over sodium sulfate and evaporated to dryness. The crude product was crystallized from ethyl acetate/heptane to yield 14.85 g of the desired product. Another 4.5 g could be obtained upon evaporation and silica gel chromatography of the mother liquor.

The precipitate was filtered and dried to yield 9.91 g of the title compound. $R_t$=1.33 min (Method B). Detected mass: 198.0 (M+H$^+$).

6-Fluoro-isoquinolinone (8)

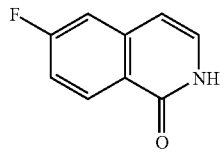 [SMILES: O=c1[nH]ccc2cc(F)ccc12]

4.8 mL (90.3 mmol, 1.5 eq.) of thionyl chloride was added portionwise to a solution of 10 g (60.2 mmol) of 3-fluoro cinnamic acid in 44 ml of chloroform and 1 ml of DMF. The reaction was heated to reflux for 2.5 h. Then the solvents were distilled to yield 11.4 g of the raw acid chloride, which was used without any further purification.

The acid chloride was dissolved in 45 mL of acetone. At 0° C. 8.03 g (123.5 mmol, 2 eq.) of NaN$_3$ were added portionwise. Then 41 mL of water were added while the temperature was kept below 5° C. The reaction was stirred for another 1.5 h. Then 55 ml of chloroform were added. The mixture was washed with 80 mL of water followed by 40 mL of brine. After drying over Na$_2$SO$_4$ and filtration, 14 mL of diphenyl ether were added and most of the chloroform was removed in vacuo (without heating). A total removal of the chloroform should be avoided.

The solution containing the azide, diphenyl ether and the remaining chloroform was added dropwise at 260° C. within 15 minutes to a solution of 10 mL of tributyl amine in 97 ml of diphenyl ether. A vigorous reaction can be observed during the addition. The reaction was stirred for another 20 minutes at 260° C. After cooling to room temperature 270 mL of n-heptane were added. The precipitated product was filtered off and washed with ether to yield 5.65 g of the title compound. MS (DCI) Detected mass: 164.0 (M+H$^+$).

6-Fluoro-2-(4-methoxy-benzyl)-2H-isoquinolin-1-one (9)

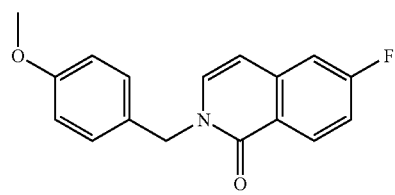 [SMILES: COc1ccc(Cn2ccc3cc(F)ccc3c2=O)cc1]

169 µL (1.24 mmol, 1.1 eq) of p-methoxybenzylchloride were added to a suspension of 200 mg (1.13 mmol) of 6-fluoro-isoquinolinone (8) and 368 mg (1.36 mmol, 1.2 eq) of Cs$_2$CO$_3$ in 3 mL of DMF. The mixture was stirred for 2 h and then poured on ice. The precipitate was filtered, washed with water and dried to yield 300 mg of the title compound. $R_t$=1.76 min (Method B). Detected mass: 284.14 (M+H$^+$).

7-Chloro-6-fluoro-2-(4-methoxy-benzyl)-2H-isoquinolin-1-one (10)

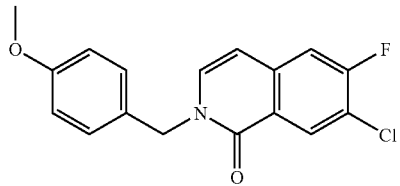 [SMILES: COc1ccc(Cn2ccc3cc(F)c(Cl)cc3c2=O)cc1]

Starting from 7-chloro-6-fluoro-2H-isoquinolin-1-one (7) the title compound was prepared following the protocol described for 6-fluoro-2-(4-methoxy-benzyl)-2H-isoquinolin-1-one (9). $R_t$=1.66 min (Method C). Detected mass: 318.3 (M+H$^+$).

1-Benzyloxy-7-chloro-6-fluoro-isoquinoline (11)

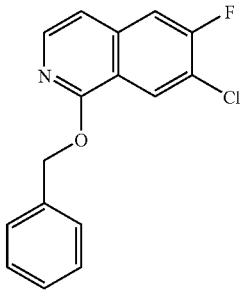 [SMILES: Fc1cc2ccnc(OCc3ccccc3)c2cc1Cl]

14.74 g (74.6 mmol) of 7-chloro-6-fluoro-2H-isoquinolin-1-one (7) were dissolved in 150 ml of toluene. After addition of 30.86 g (111.9 mmol) of silver carbonate and 15.31 g (89.5 mmol) of benzyl bromide, the mixture was stirred at 80° C. for 3 h. After cooling down to room temperature, the reaction mixture was filtered and the filtrate was evaporated. The residue was dissolved in dichloromethane and washed with water, dried with magnesium sulfate and evaporated. Final purification by preparative HPLC gave 11.63 g of the title compound. $R_t$=2.51 min (Method B). Detected mass: 288.1/290.1 (M+H$^+$).

6-(cis-4-Amino-cyclohexyloxy)-7-chloro-2H-isoquinolin-1-one (12)

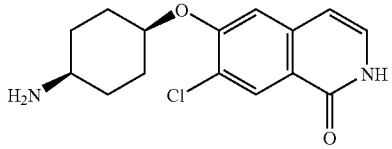

2.19 g (10.2 mmol) of cis-(4-hydroxy-cyclohexyl)-carbamic acid tert-butyl ester were dissolved in 20 ml of dimethyl acetamide. Under argon atmosphere, 814 mg (20.4 mmol) of sodium hydride (60%) were added and the mixture was stirred at room temperature. After 30 min, a solution of 2.0 g (9.26 mmol) of 1,7-dichloro-6-fluoro-isoquinoline (6) in 5 ml of dimethyl acetamide was added and stirring was continued at room temperature. After 1 h, 2.0 g (18.5 mmol) of benzyl alcohol and 740 mg (18.5 mmol) of sodium hydride (60%) were added. The reaction was stirred for 2 h at room temperature and 30 minutes at 80° C. to achieve complete conversion. The solvent was removed in vacuo and the residue was taken up in dichloromethane and washed twice with water. After drying over magnesium sulfate, the organic layer was evaporated, to furnish 4.44 g of the crude intermediate cis-[4-(1-benzyloxy-7-chloro-isoquinolin-6-yloxy)-cyclohexyl]-carbamic acid tert-butyl ester. The intermediate was dissolved in methanol and treated with 2 N HCl at room temperature. After stirring for 2 d, the reaction mixture was adjusted to alkaline pH by addition of sodium hydroxide. The solvent was removed in vacuo and the residue was stirred in ethanol. Filtration and evaporation of the filtrate yielded a solid material, which was purified by preparative HPLC. The obtained trifluoroacetate was dissolved in 2 N HCl. Final lyophilization gave 433 mg of the title compound as hydrochloride. $R_t$=0.89 min (Method B). Detected mass: 293.2/295.2 (M+H$^+$).

1-Benzyloxy-7-chloro-6-(1,4-dioxa-spiro[4.5]dec-8-yloxy)-isoquinoline (13)

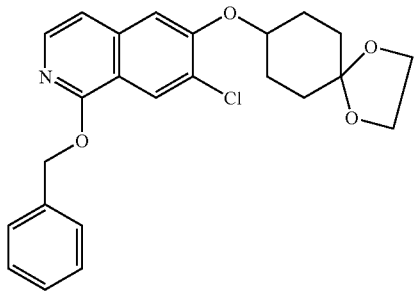 [SMILES: Clc1cc2c(OCc3ccccc3)nccc2cc1OC1CCC2(CC1)OCCO2]

1.26 g (8.34 mmol) of dioxa-spiro[4.5]decan-8-ol were dissolved in 50 ml of dimethyl acetamide and 695.2 mg (17.4 mmol) of sodium hydride (60%) were added. After stirring for 30 minutes at room temperature a solution of 2.0 g (6.95 mmol) of 1-benzyloxy-7-chloro-6-fluoro-isoquinoline (11) in 50 ml of dimethyl acetamide was added and stirring was continued at room temperature. After 1 h the solvent was removed under reduced pressure. The residue was dissolved in dichloromethane and washed with water. The organic layer was dried with magnesium sulfate and evaporated, which gave 3.30 g of the crude product, which was used without further purification. $R_t$=2.05 min (Method C). Detected mass: 426.5 (M+H$^+$).

7-Chloro-6-(4-oxo-cyclohexyloxy)-2H-isoquinolin-1-one (14)

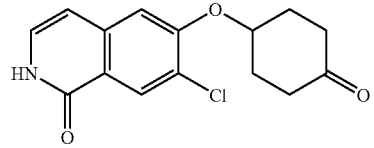 [SMILES: O=C1CCC(Oc2cc3cc[nH]c(=O)c3cc2Cl)CC1]

3.30 g of 1-benzyloxy-7-chloro-6-(1,4-dioxa-spiro[4.5]dec-8-yloxy)-isoquinoline (13, crude product) were stirred in 30 ml of 6 N HCl/acetone (1:2) at room temperature. After 3 h the reaction mixture was poured on saturated sodium bicarbonate solution and extracted with dichloromethane. The organic layer was dried with magnesium sulfate and evaporated. The crude product was purified by preparative HPLC. $R_t$=1.34 min (Method B). Detected mass: 292.0 (M+H$^+$).

Starting from 7-chloro-6-(4-oxo-cyclohexyloxy)-2H-isoquinolin-1-one (14), the following compounds were synthesized as hydrochlorides in analogy to the general procedure described below:

General Procedure for the Reductive Amination Reaction:

0.46 mmol of a suitable amine were dissolved in 10 ml of methanol. After addition of molecular sieves 4 Å, 92.3 mg (0.57 mmol) of triethyl amine, 273.8 mg (4.56 mmol) of acetic acid and 0.57 mmol of the ketone (14), a solution of 86.0 mg (1.37 mmol) of sodium cyano borohydride was added dropwise and the mixture was stirred at room temperature until complete conversion was achieved. In some cases it was necessary to heat the mixture to 70° C. to achieve complete conversion. For the isolation of the products the solution was filtered and the solvent was removed under reduced pressure. The residue was dissolved in dichloromethane, washed with 1 N NaOH and sat. sodium chloride solution, dried with magnesium sulfate and evaporated. The mono- or bis alkylated products, if obtained, were purified by preparative HPLC or precipitated from methanolic HCl.

The obtained trifluoroacetates were stirred in 2 N HCl/methanol, evaporated, dissolved in water and freeze dried to yield the desired products as hydrochlorides. Boc-protected products were deprotected during the evaporation of the HPLC-product fractions, which contained 0.1% TFA, or during the subsequent stirring in 2 N HCl/methanol. See Table 1

TABLE 1

| Example | Amine | Product | Remark | Chemical name | [M + H⁺]/ [g/ mol] | $R_t$/ [min] | Method |
|---|---|---|---|---|---|---|---|
| 15 | (piperidine-4-carboxamide) | (structure) | cis/ trans-mixture | 1-[4-(7-Chloro-1-oxo-1,2-di-hydro-isoquino-lin-6-yloxy)-cyclohexyl]-piperidine-4-carboxylic acid amide | 404.1 | 0.92 | B |
| 16 | (piperidine) | (structure) ClH | cis/ trans-mixture | 7-Chloro-6-(4-piperidin-1-yl-cyclohexyloxy)-2H-isoquinolin-1-one | 361.1 | 1.08 | B |
| 17 | (morpholine) | (structure) | trans-isomer isolated by stirring the crude product of the red. aminat. with 2 N HCl. Filtration of the precipitate gave pure trans-isomer. | 7-Chloro-6-(4-morpholin-4-yl-cyclohexyloxy)-2H-isoquinolin-1-one | 363.2 | 1.07 | B |
| 18 | (morpholine) | (structure) | Mother liquor from example 17 was purified by prep. HPLC, by which a 2:1 ratio (cis:trans) was obtained. | 7-Chloro-6-(4-morpholin-4-yl-cyclohexyloxy)-2H-isoquinolin-1-one | 363.1 | 0.95 | B |
| 19 | (pyrrolidine) | (structure) | cis- and trans isomers separated by prep. HPLC; trans-isomer obtained in approx. 80% purity. | 7-Chloro-6-(4-pyrrolidin-1-yl-cyclohexyloxy)-2H-isoquinolin-1-one | 347.1 | 1.02 | B |

TABLE 1-continued

| Example | Amine | Product | Remark | Chemical name | [M + H⁺]/ [g/mol] | $R_t$/[min] | Method |
|---|---|---|---|---|---|---|---|
| 20 | | | cis- and trans isomers separated by prep. HPLC; cis-isomer obtained in >95% purity. | 7-Chloro-6-(4-pyrrolidin-1-yl-cyclohexyloxy)-2H-isoquinolin-1-one | 347.1 | 0.97 | B |
| 21 | | | cis- and trans isomers separated by prep. HPLC; trans-isomer obtained in approx. 80% purity. | 7-Chloro-6-[4-(4-methyl-piperazin-1-yl)-cyclohexyloxy]-2H-isoquinolin-1-one | 376.2 | 0.81 | B |
| 22 | | | cis- and trans isomers separated by prep. HPLC; cis-isomer obtained in approx. 75% purity | 7-Chloro-6-[4-(4-methyl-piperazin-1-yl)-cyclohexyloxy]-2H-isoquinolin-1-one | 376.1 | 0.82 | B |

[4-(7-Chloro-1-oxo-1,2-dihydro-isoquinolin-6-yloxy)-cis-cyclohexylamino]-acetic acid ethyl ester (23)

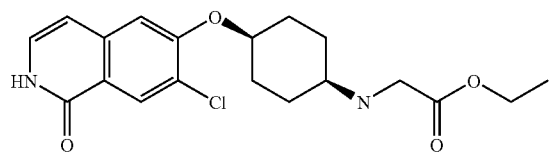 [SMILES: CCOC(=O)CN[C@H]1CC[C@@H](Oc2cc3cc[nH]c(=O)c3cc2Cl)CC1]

300 mg (0.91 mmol) of 6-cis-(4-amino-cyclohexyloxy)-7-chloro-2H-isoquinolin-1-one (12) were dissolved in 20 ml of methanol and treated with 258 mg (1.14 mmol) glyoxylic acid ethyl ester following the general method for reductive amination reactions. To achieve complete conversion, additional 5.0 equivalents of glyoxylic acid ethyl ester and 0.5 equivalents sodium cyano borohydride were added portionwise over 34 h and the temperature was increased to 60° C. after 5 h reaction time until the reaction went to completion. After filtration, the reaction solution was evaporated. The residue was dissolved in dichloromethane, washed with 1 N NaOH and saturated NaCl-solution, dried over MgSO₄ and evaporated. The so obtained crude product was used in the next reaction without further purification. $R_t$=0.81 min (Method C). Detected mass: 365.4 (M+H⁺, methyl ester, because methanol was used as solvent), 0.87 min. (Method C). Detected mass: 379.4 (M+H⁺, ethyl ester, title compound).

[4-(7-Chloro-1-oxo-1,2-dihydro-isoquinolin-6-yloxy)-cis-cyclohexylamino]-acetic acid (24)

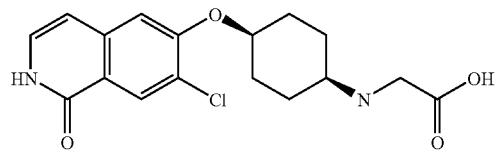 [SMILES: O=C(O)CN[C@H]1CC[C@@H](Oc2cc3cc[nH]c(=O)c3cc2Cl)CC1]

185 mg of [4-(7-chloro-1-oxo-1,2-dihydro-isoquinolin-6-yloxy)-cis-cyclohexylamino]-acetic acid ethyl ester (23, crude product) were dissolved in 2 ml methanol. After adding 2 ml of 2 N NaCO₃-solution, the solution was stirred at room temperature for 1.5 h. The solvent was evaporated in vacuo and the residue was purified by preparative HPLC, which delivers the title compound as trifluoro acetate. $R_t$=0.91 min (Method B). Detected mass: 351.3 (M+H⁺).

6-(trans-4-Amino-cyclohexyloxy)-7-methyl-2H-isoquinolin-1-one (25)

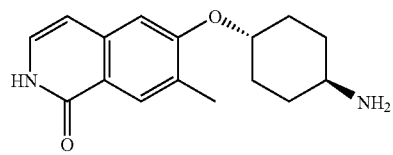 [SMILES: Cc1cc2c(=O)[nH]ccc2cc1O[C@H]1CC[C@H](N)CC1]

a) 6-Fluoro-7-methyl-2H-isoquinolin-1-one

To a solution of 10.0 g (55.5 mmol) of 3-fluoro-4-methyl-cinnamic acid in 80 ml of acetone were subsequently added at 0° C. 6.74 g (66.6 mmol) of triethylamine in 10 ml of acetone followed by 7.83 g (72.2 mmol) of ethyl chloroformate. After stirring for 2 h at 0 to 5° C., a solution of 4.0 g (61.1 mmol) of sodium azide in 9.5 ml of water was added. After stirring for 1 additional h the reaction mixture was poured onto 200 ml of ice water and extracted twice with chloroform. The organic phase was dried over magnesium sulfate, 40 ml diphenylether were added and the chloroform was cautiously removed in vacuo. The residue was then added dropwise into 50 ml of diphenylether, which had been preheated to 245° C. After complete addition it was stirred for another 1 h at 230-250° C. After cooling down to 150° C. the reaction mixture was poured into 270 ml of heptane and after further cooling in an ice bath the precipitated product was filtered by suction and 4.1 g 6-fluoro-7-methyl-2H-isoquinolin-1-one were obtained.

b) 6-Fluoro-2-(4-methoxy-benzyl)-7-methyl-2H-isoquinolin-1-one

To a solution of 9.17 g (51.8 mmol) of 6-fluoro-7-methyl-2H-isoquinolin-1-one in 80 ml of DMF were added 20.2 g (62.1 mmol) of cesium carbonate and then 8.92 g (56.9 mmol) of 4-methoxybenzylchloride. After stirring at room temperature for 90 minutes the reaction mixture was poured into 600 ml of water, stirred for 1 h, and then the precipitated product was isolated by suction. From the mother liquor additional product was isolated by chromatography with heptane/ethyl acetate (80:20). The combined products were recrystallized from ethyl acetate and 8.39 g of 6-fluoro-2-(4-methoxy-benzyl)-7-methyl-2H-isoquinolin-1-one were obtained.

c) 6-(trans-4-Amino-cyclohexyloxy)-2-(4-methoxy-benzyl)-7-methyl-2H-isoquinolin-1-one To a solution of 1.48 g (9.75 mmol) of trans-4-aminocyclohexanol hydrochloride in 20 ml of dimethylacetamide were added 1.95 g (48.77 mmol) of sodium hydride (60%) and the mixture was stirred for 15 minutes. Subsequently 2.90 g (9.75 mmol) of 6-fluoro-2-(4-methoxy-benzyl)-7-methyl-2H-isoquinolin-1-one in 30 ml of dimethylacetamide were added and the reaction mixture was heated to 80° C. for 2 days. After cooling, the mixture was poured into 300 ml of ice water and the precipitated crude product was purified by chromatography. First the remaining starting material was eluted with ethyl acetate/heptane (2:1) and finally the desired product was eluted by pure methanol giving 1.98 g 6-(trans-4-amino-cyclohexyloxy)-2-(4-methoxy-benzyl)-7-methyl-2H-isoquinolin-1-one.

d) 6-(trans-4-Amino-cyclohexyloxy)-7-methyl-2H-isoquinolin-1-one (25)

2.64 g (6.7 mmol) of 6-(trans-4-amino-cyclohexyloxy)-2-(4-methoxy-benzyl)-7-methyl-2H-isoquinolin-1-one and 15.3 g (134.5 mmol) of trifluoroacetic acid were heated for 2 h in a microwave oven at 150° C. Then the excess trifluoroacetic acid was distilled off in vacuo and the residue was diluted with 130 ml of 1 M hydrochloric acid. The aqueous phase was washed with dichloromethane 3 times and then it was freeze dried to give the hydrochloride, which was recrystallized from isopropanol. This furnished 1.1 g 6-(trans-4-amino-cyclohexyloxy)-7-methyl-2H-isoquinolin-1-one (25) as hydrochloride. $R_t$=0.92 min (Method B). Detected mass: 273.22 (M+H$^+$).

6-(cis-4-Amino-cyclohexyloxy)-7-methyl-2H-isoquinolin-1-one (26)

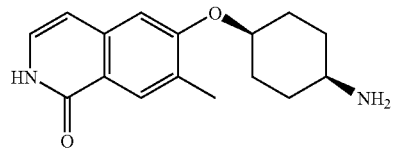 [SMILES: Cc1cc2c(=O)[nH]ccc2cc1O[C@H]1CC[C@@H](N)CC1]

a) cis-4-Aminocyclohexanol

To a solution of 30.0 g (0.265 mol) of cyclohexanone oxime in 300 ml of dichloromethane and 38 ml of ethanol was slowly added at 0° C. 34.5 g (0.318 mol) of tert.-butyl-hypochlorite. The resulting dark blue solution was cooled to −20° C. and then 31.9 g (0.398 mol) of 1,3-cyclohexadiene were added and the mixture was stored in a freezer at 5° C. for 2 days until the blue color had disappeared. The reaction mixture was concentrated to 50% of its volume and then 600 ml of diethyl ether were slowly added. After stirring overnight the resulting precipitate was isolated by suction to yield 29.0 g of 2-oxa-3-aza-bicyclo[2.2.2]oct-5-ene as hydrochloride. 5.0 g (0.045 mol) of this material were hydrogenated with 3.0 g (0.013 mol) platinum oxide at 2 bar hydrogen pressure. After 7 h the catalyst was filtered off and a solution of 20 ml 4 M hydrochloric acid in dioxane was added. After evaporation the residue was recrystallized from 30 ml isopropanol giving 3.1 g of cis-4-aminocyclohexanol as hydrochloride.

b) 6-(cis-4-Aminocyclohexyloxy)-7-methyl-2H-isoquinolin-1-one (26)

From 2.55 g (16.8 mmol) of cis-4-aminocyclohexanol hydrochloride and 5.0 g (16.8 mmol) of 6-fluoro-2-(4-methoxy-benzyl)-7-methyl-2H-isoquinolin-1-one (25, step b) were prepared 0.98 g of 6-(cis-4-amino-cyclohexyloxy)-7-methyl-2H-isoquinolin-1-one hydrochloride as described in example 25 (steps c and d). $R_t$=0.99 min (Method B). Detected mass: 273.18 (M+H$^+$).

7-Methyl-6-(4-pyrrolidin-1-yl-cyclohexyloxy)-2H-isoquinolin-1-one (27)

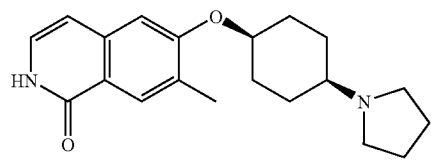 [SMILES: Cc1cc2c(=O)[nH]ccc2cc1O[C@H]1CC[C@@H](N2CCCC2)CC1]

a) 2-(4-Methoxy-benzyl)-7-methyl-6-(4-pyrrolidin-1-yl-cyclohexyloxy)-2H-isoquinolin-1-one To a solution of 0.4 g (1 mmol) of 6-(cis-4-amino-cyclohexyloxy)-2-(4-methoxy-benzyl)-7-methyl-2H-isoquinolin-1-one (26, step b), 0.31 g (2 mmol) sodium iodide and 0.35 g (2.5 mmol) potassium carbonate in 40 ml DMF were added dropwise 0.24 g (1.1 mmol) 1,4-dibromobutane. After stirring at room temperature for 2 days the mixture was diluted with water and extracted with ethyl acetate. After drying and evaporation the residue was purified by chromatography to yield 182 mg of 2-(4-methoxy-benzyl)-7-methyl-6-(4-pyrrolidin-1-yl-cyclohexyloxy)-2H-isoquinolin-1-one.

b) 7-Methyl-6-(4-pyrrolidin-1-yl-cyclohexyloxy)-2H-isoquinolin-1-one (27)

180 mg (0.4 mmol) of 2-(4-methoxy-benzyl)-7-methyl-6-(4-pyrrolidin-1-yl-cyclohexyloxy)-2H-isoquinolin-1-one were heated with 0.9 g trifluoro acetic acid in a microwave oven at 150° C. After aqueous workup, 58 mg of 7-methyl-6-(4-pyrrolidin-1-yl-cyclohexyloxy)-2H-isoquinolin-1-one were obtained as hydrochloride. $R_t$=1.07 min (Method B). Detected mass: 327.2 (M+H$^+$).

General Procedure for Amide Formation:

0.6 mmol of a suitable amine (as hydrochloride) were suspended in 7.5 mL of dry DMF. After cooling to 0° C., 0.6 mmol of triethylamine and 0.6 mmol of O-((ethoxycarbonyl)cyanomethyleneamino)-N,N,N',N'-tetramethyluronium tetrafluoroborate) were added. This solution was added to a solution of the corresponding carboxylic acid (0.6 mmol) and 1 eq. of triethylamine in 7.5 mL of DMF. The mixture was warmed to room temperature and stirred for 2 h. The progression of reaction was monitored by HPLC and if necessary, an additional equivalent of TOTU and triethylamine was added. The mixture was evaporated, the crude product was taken up in ethyl acetate and filtered over celite, and the solvent was evaporated. The product was purified by silica gel chromatography.

The resulting product was dissolved in 10 mL of dichloromethane and trifluoro acetic acid (1 mL) was added. The mixture was stirred for 2 h at ambient temperature, evaporated, taken up in 1 M HCl and lyophilized. Final double dissolution of the crude product in water, followed by lyophilization yielded the desired product as the hydrochloride.

TABLE 2

| Example | Amine | Aldehyde | Product | [M + H$^+$] | $R_t$/[min] | Method | Chemical Name |
|---|---|---|---|---|---|---|---|
| 28 | 25 | (structure) | (structure) | 412.4 | 1.07 | B | N-[4-(7-Methyl-1-oxo-1,2-dihydro-isoquinolin-6-yloxy)-trans-cyclohexyl]-3-piperidin-4-yl-propionamide |
| 29 | 25 | (structure) | (structure) | 397.2 | 1.01 | B | N-[4-(7-Methyl-1-oxo-1,2-dihydro-isoquinolin-6-yloxy)-trans-cyclohexyl]-2-piperidin-4-yl-acetamide |
| 30 | 12 | (structure) | (structure) | 432.2 | 1.06 | B | N-[4-(7-Chloro-1-oxo-1,2-dihydro-isoquinolin-6-yloxy)-cis-cyclohexyl]-3-piperidin-4-yl-propionamide |

TABLE 2-continued

| Example | Amine | Aldehyde | Product | [M + H⁺] | $R_t$/ [min] | Method | Chemical Name |
|---|---|---|---|---|---|---|---|
| 31 | 12 | 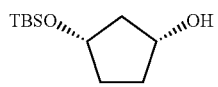 |  | 418.3 | 1.02 | B | N-[4-(7-Chloro-1-oxo-1,2-dihydro-iso-quinolin-6-yloxy)-cis-cyclo-hexyl]-2-piperidin-4-yl-acetamide |

(1R,3S)-3-(tert-Butyl-dimethyl-silanyloxy)-cyclo-pentanol (32)

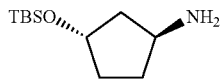 [SMILES: CC(C)(C)[Si](C)(C)O[C@H]1CC[C@H](N)C1]

A solution of 2.0 g (9.33 mmol) of (1S,4R)-4-(tert-butyl-dimethyl-silanyloxy)-cyclopent-2-enol (Curran, et al. Tetrahedron 1997, 53, 1983-2004) in 10 mL of ethyl acetate was treated with 66 mg of 20% palladium hydroxide on activated carbon and the mixture was stirred overnight under a hydrogen atmosphere (1 atm) at room temperature. The catalyst was removed by filtration, and the filtrate was evaporated in vacuo to give 2.0 g of the title compound (32). $R_t$=1.72 min (Method C). Detected mass: 217.2 (M+H⁺).

(1S,3S)-3-(tert-Butyl-dimethyl-silanyloxy)-cyclo-pentylamine (33)

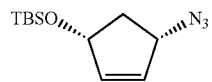

720 mg (3.33 mmol) of (1R,3S)-3-(tert-butyl-dimethyl-silanyloxy)-cyclopentanol (32) and 2.18 g (8.32 mmol) of triphenylphosphine were dissolved in 15 mL of tetrahydrofuran and cooled to −20° C. Then, 1.05 mL (6.65 mmol) of diethylazodicarboxylate, and after 3 min, 717 μL (3.33 mmol) of diphenylphosphoryl azide were added dropwise and the mixture was stirred at room temperature overnight. Diethylether and sat. sodium chloride solution were added and the aqueous phase was extracted three times with diethylether. The combined organic layers were dried over sodium sulfate, filtered and evaporated.

The crude product was dissolved in 15 mL of tetrahydrofuran and 1.47 g (1.80 mmol) of triphenylphosphine on polystyrene (1.2 mmol/g) were added. After the addition of 2 mL of water, the reaction mixture was stirred at room temperature until the reaction was complete. The resin was removed by filtration, and the filtrate was evaporated in vacuo. The obtained product, 256 mg of the title compound (33), was sufficiently pure for further conversion. $R_t$=1.11 min (Method C). Detected mass: 216.2 (M+H⁺).

(1S,3S)-3-Amino-cyclopentanol (34)

To a solution of 95 mg (0.44 mmol) of (1S,3S)-3-(tert-butyl-dimethyl-silanyloxy)-cyclopentylamine (33) in 1 mL of 2-propanol was added 1 mL of 2N hydrochloric acid and the mixture was stirred at room temperature until complete conversion was achieved. The reaction mixture was washed three times with diethylether, the aqueous phase was concentrated in vacuo and lyophilized. The residue was taken up in water and lyophilized again, to yield 68 mg of (1S,3S)-3-amino-cyclopentanol (34) as hydrochloride. $R_t$=0.13 min (Method C). Detected mass: 102.3 (M+H⁺).

((1R,4S)-4-Azido-cyclopent-2-enyloxy)-tert-butyl-dimethyl-silane (35)

The title compound was prepared by combining a solution of 630 mg (2.46 mmol) of acetic acid (1S,4R)-4-(tert-butyl-dimethyl-silanyloxy)-cyclopent-2-enyl ester [synthesized by silylation of commercially available acetic acid (1S,4R)-4-hydroxy-cyclopent-2-enyl ester (Curran, et al. Tetrahedron 1997, 53, 1983-2004)] in 6 mL tetrahydrofuran with a solution of 320 mg (4.91 mmol) of sodium azide in 1.3 mL of water. To this biphasic mixture was added a solution of 112 mg (0.12 mmol) of tris(dibenzylideneacetone)dipalladium (0) and 258 mg (0.98 mmol) of triphenylphosphine in 2 mL tetrahydrofuran, and the reaction mixture was heated to 50° C. for 6 h, when the reaction was complete. Sat. sodium chloride solution was added, and the aqueous phase was repeatedly extracted with ether. The combined organic phase was dried over sodium sulfate, filtered and evaporated. The crude material was purified by silica gel chromatography to yield 475 mg of the title compound (35). ¹H NMR (400 MHz, DMSO) δ=0.09 (s, 3H), 0.10 (s, 3H), 0.88 (s, 9H), 1.49 (dt, J=3.9, 14.0 Hz, 1H), 2.69 (dt, J=7.4, 14.1 Hz, 1H), 4.22-4.26 (m, 1H), 4.75-4.79 (m, 1H), 5.92-5.95 (m, 1H), 6.05 (dt, J=1.8, 5.4 Hz, 1H)

(1S,4R)-4-(tert-Butyl-dimethyl-silanyloxy)-cyclopent-2-enylamine (36)

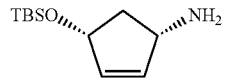

934 mg (3.90 mmol) of ((1R,4S)-4-azido-cyclopent-2-enyloxy)-tert-butyl-dimethyl-silane (35) were dissolved in 16 mL of tetrahydrofuran and 1.13 g (4.29 mmol) of triphenylphosphine were added. After the addition of 2 mL of water, the reaction mixture was stirred at room temperature, until the reaction was complete. Sat. sodium chloride solution was added, the layers separated and the organic layer was evaporated in vacuo. The crude product was purified by silica gel chromatography to yield 890 mg of the title compound (36). $R_t$=1.02 min (Method C). Detected mass: 214.3 (M+H$^+$).

(1R,3S)-3-(tert-Butyl-dimethyl-silanyloxy)-cyclopentylamine (37)

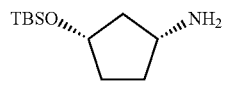

Method A

To a solution of 135 mg (0.56 mmol) of ((1R,4S)-4-azido-cyclopent-2-enyloxy)-tert-butyl-dimethyl-silane (35) in 2 mL methanol was added 60 mg of 5% palladium on activated carbon, and the suspension was stirred under a hydrogen atmosphere (1 atm) at room temperature overnight. The catalyst was removed by filtration, and the filtrate was evaporated in vacuo. The residue was purified by silica gel chromatography to yield 98 mg of the title compound (37). $R_t$=1.15 min (Method C). Detected mass: 216.3 (M+H$^+$).

Method B

A solution of 330 mg (1.55 mmol) of (1S,4R)-4-(tert-butyl-dimethyl-silanyloxy)-cyclopent-2-enylamine (36) in 4 mL of ethanol was treated with 164 mg of 5% palladium on activated carbon, and the mixture was stirred under a hydrogen atmosphere (1 atm) at room temperature for 5 h. The catalyst was removed by filtration, and the filtrate was evaporated to give 227 mg of the title compound (37) in purity sufficient for further conversion.

(1S,3R)-3-Amino-cyclopentanol (38)

Starting from 486 mg (2.26 mmol) of (1R,3S)-3-(tert-butyl-dimethyl-silanyloxy)-cyclopentylamine (37), 229 mg of the title compound were synthesized as hydrochloride following the protocol described for (1S,3S)-3-amino-cyclopentanol (34). $R_t$=0.14 min (Method C). Detected mass: 102.3 (M+H$^+$).

2-(4-Methoxy-benzyl)-6-((1S,3S)-3-amino-cyclopentyloxy)-2H-isoquinolin-1-one (39)

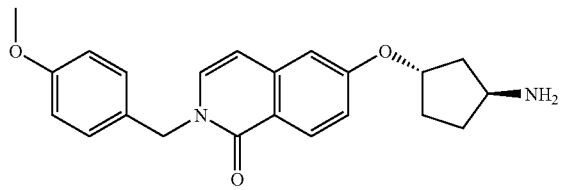 [SMILES: COc1ccc(Cn2ccc3cc(O[C@H]4CC[C@@H](N)C4)ccc3c2=O)cc1]

106 mg (4.20 mmol) of sodium hydride (95%) were suspended in 3 mL of dimethyl acetamide and 193 mg (1.40 mmol) of (1S,3S)-3-amino-cyclopentanol (34), dissolved in 1 mL of dimethyl acetamide, were added dropwise. After 1 h, 402 mg (1.42 mmol) of 2-(4-methoxy-benzyl)-6-fluoro-2H-isoquinolin-1-one (9), dissolved in another 3 mL of dimethyl acetamide, were added. The reaction mixture was stirred at 80° C. until the reaction was complete. The mixture was poured into water, extracted three times with a mixture of dichloromethane and 2-propanol (3:1) and the combined organic layers were evaporated. Water was added and the crude product was subjected to lyophilization to remove remainders of dimethyl acetamide. The obtained crude product was purified by silica gel chromatography to yield 250 mg of the title compound (39). $R_t$=1.20 min (Method E). Detected mass: 365.2 (M+H$^+$).

The following three products were obtained by the same procedure described for the synthesis of 39 using the corresponding 2-(4-methoxy-benzyl)-6-fluoro-2H-isoquinolin-1-ones and 3-amino-cyclopentanols. Table 3

TABLE 3

| Example | Isoquinolinone | Amine | Product | Chemical Name | [M + H$^+$] | $R_t$/[min] | Method |
|---------|----------------|-------|---------|---------------|-------------|-------------|--------|
| 40 | 10 | 34 | | 2-(4-Methoxy-benzyl)-6-((1S,3S)-3-amino-cyclopentyloxy)-7-chloro-2H-isoquinolin-1-one | 399.1 | 1.32 | E |

TABLE 3-continued

| Example | Isoquinolinone | Amine | Product | Chemical Name | [M + H⁺] | $R_t$/[min] | Method |
|---|---|---|---|---|---|---|---|
| 41 | 9 | 38 | | 2-(4-Methoxy-benzyl)-6-((1S,3R)-3-amino-cyclo-pentyloxy)-7-chloro-2H-iso-quinolin-1-one | 365.2 | 1.23 | E |
| 42 | 10 | 38 | | 2-(4-Methoxy-benzyl)-6-((1S,3R)-3-amino-cyclo-pentyloxy)-7-chloro-2H-isoquinolin-1-one | 399.1 | 1.25 | E |

6-((1S,3S)-3-Amino-cyclopentyloxy)-2H-isoquinolin-1-one (43)

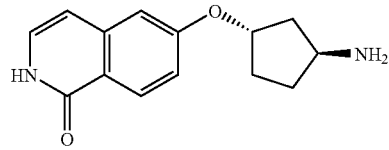 [SMILES: N[C@H]1CC[C@H](Oc2ccc3c(=O)[nH]ccc3c2)C1]

125 mg (0.34 mmol) of 2-(4-methoxy-benzyl)-6-((1S,3S)-3-amino-cyclopentyloxy)-2H-isoquinolin-1-one (39) were dissolved in 1 mL of TFA and heated in a microwave oven at 150° C. for 3 h. Methanol was added and the reaction mixture was evaporated. The solution was taken up in 1N HCl and extracted three times with dichloromethane. The combined dichloromethane layers were extracted with 1N HCl twice and the combined HCl layers were lyophilized. The residue was dissolved in water and lyophilized again to yield 42 mg of 6-((1S,3S)-3-amino-cyclopentyloxy)-2H-isoquinolin-1-one (43) as hydrochloride. $R_t$=0.86 min (Method E). Detected mass: 245.1 (M+H⁺).

The following three products were obtained as hydrochlorides by the same procedure described for the synthesis of 43 starting from the corresponding 2-(4-methoxy-benzyl)-2H-isoquinolin-1-ones (Table 4)

TABLE 4

| Example | Starting comp. | Product | Chemical name | [M + H⁺] | $R_t$/[min] | Method |
|---|---|---|---|---|---|---|
| 44 | 40 | | 6-((1S,3S)-3-Amino-cyclo-pentyloxy)-7-chloro-2H-isoquinolin-1-one | 279.1 | 1.00 | F |
| 45 | 41 | | 6-((1S,3R)-3-Amino-cyclo-pentyloxy)-2H-isoquinolin-1-one | 245.2 | 0.64 | C |
| 46 | 42 | | 6-((1S,3R)-3-Amino-cyclo-pentyloxy)-7-chloro-2H-isoquinolin-1-one | 279.1 | 0.90 | E |

6-(cis-4-Amino-cycloheptyloxy)-7-methyl-2H-isoquinolin-1-one (47)

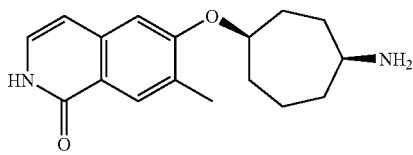 [SMILES: Cc1cc2c(=O)[nH]ccc2cc1O[C@@H]1CCC[C@H](N)CC1]

a) cis-4-Amino-cycloheptanol

To a solution of 16.8 g (0.149 mol) cyclohexanone oxime in 240 ml methylene chloride was slowly added at 0° C. 19.4 g (0.178 mol) tert.-butyl-hypochlorite. The resulting dark blue solution was cooled to −20° C. and then 30 ml ethanol and 20.0 g (0.212 mol) 1,3-cycloheptadiene were added and the mixture was stored in a freezer at 5° C. for 2 days until the blue color had disappeared. The reaction mixture was added to 30 ml isopropanol and then 300 ml diethyl ether and after stirring for 3 h the resulting precipitate was isolated by suction to yield 18.6 g of 6-oxa-7-aza-bicyclo[3.2.2]non-8-ene hydrochloride. 9.0 g (0.072 mol) of this material were hydrogenated with palladium on activated carbon at 5 bar hydrogen. After complete conversion the catalyst was filtered off and a solution of 30 ml 4 M hydrochloric acid in dioxane was added. After evaporation the residue was crystallized from 20 ml isopropanol and 500 ml diethyl ether giving 7.5 g cis-4-amino-cycloheptanol as hydrochloride.

b) 6-(cis-4-Amino-cycloheptyloxy)-2-(4-methoxy-benzyl)-7-methyl-2H-isoquinolin-1-one A solution of 223 mg (1.35 mmol) cis-4-amino-cycloheptanol in 5 ml dimethylacetamide was stirred with 242 mg (8.1 mmol) 80% sodium hydride for 15 minutes at room temperature. Then a solution of 0.4 g (1.35 mmol) 6-fluoro-2-(4-methoxy-benzyl)-7-methyl-2H-isoquinolin-1-one (25, step b) in 10 ml dimethylacetamide was added. The reaction mixture was heated to 80° C. for 8 h after which time additional 30% of the original amounts of cis-4-amino-cycloheptanol and sodium hydride were added. After further 8 h at 80° C. the reaction mixture was added to water and extracted with dichloromethane. Purification of the crude product by chromatography with dichloromethane/methanol (100:0-97:3) delivered 134 mg of 6-(cis-4-amino-cycloheptyloxy)-2-(4-methoxy-benzyl)-7-methyl-2H-isoquinolin-1-one.

c) 6-(cis-4-Amino-cycloheptyloxy)-7-methyl-2H-isoquinolin-1-one (47)

130 mg (0.32 mmol) 6-(cis-4-amino-cycloheptyloxy)-2-(4-methoxy-benzyl)-7-methyl-2H-isoquinolin-1-one were dissolved in 730 mg (6.4 mmol) trifluoroacetic acid and the mixture was heated for 2 h in a microwave oven at 150° C. Then the excess trifluoroacetic acid was distilled off in vacuo and the residue was diluted with water and the solution was made alkaline. After extraction with dichloromethane, drying over magnesium sulfate and evaporation 24 mg of 6-(cis-4-amino-cycloheptyloxy)-7-methyl-2H-isoquinolin-1-one (47) were obtained. $R_f$=0.96 min (Method B). Detected mass: 287.3 (M+H$^+$).

7-Chloro-6-(cis-4-Amino-cycloheptyloxy)-2H-isoquinolin-1-one (48)

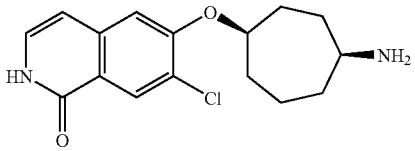 [SMILES: N[C@H]1CCC[C@@H](Oc2cc3cc[nH]c(=O)c3cc2Cl)CC1]

The title product was obtained as hydrochloride in a similar fashion as described for the synthesis of 6-(cis-4-amino-cycloheptyloxy)-7-methyl-2H-isoquinolin-1-one (47), using cis-4-amino-cycloheptanol hydrochloride (47, step a) and 7-chloro-6-fluoro-2-(4-methoxy-benzyl)-2H-isoquinolin-1-one (10). $R_f$=1.05 min (Method B). Detected mass: 307.12 (M+H$^+$).

6-(cis-4-Amino-cycloheptyloxy)-2H-isoquinolin-1-one (49)

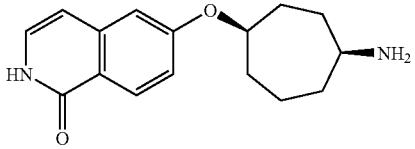 [SMILES: N[C@H]1CCC[C@@H](Oc2ccc3c(=O)[nH]ccc3c2)CC1]

The title product was obtained as hydrochloride in a similar fashion as described for the synthesis of 6-(cis-4-amino-cycloheptyloxy)-7-methyl-2H-isoquinolin-1-one (47), using cis-4-amino-cycloheptanol hydrochloride (47, step a) and 6-fluoro-2-(4-methoxy-benzyl)-2H-isoquinolin-1-one (9). $R_f$=0.81 min (Method C). Detected mass: 273.2 (M+H$^+$).

3-Amino-cyclobutanol (50)

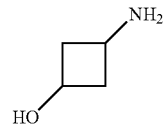

To a 0° C. cold solution of 2.00 g (10.8 mmol) of (3-oxo-cyclobutyl)-carbamic acid tert-butyl ester in 20 mL of ethanol was added portionwise 204 mg (5.40 mmol) of sodium borohydride. The reaction mixture was stirred at room temperature until complete conversion was achieved. The solvent was evaporated, the crude product was taken up in dichloromethane and treated with sat. sodium bicarbonate solution. The phases were separated and the aqueous phase extracted twice with dichloromethane. The organic phases were combined, dried over magnesium sulfate and concentrated to give crude (3-hydroxy-cyclobutyl)-carbamic acid tert-butyl ester. $R_f$=0.76 min (Method C). Detected mass: 132.2 (M-tBu+H$^+$).

The crude alcohol was dissolved in 90 mL of dichloromethane and 11 mL of trifluoroacetic acid were added. After stirring overnight at room temperature, 100 mL of 2N hydrochloric acid were added, the phases were separated and the aqueous phase concentrated in vacuo. After twice dissolving the residue in water and subsequent lyophilization, 980 mg of the title compound 50 were isolated as its hydrochloride as a mixture of diastereoisomers. $R_t$=0.19 min (Method C). Detected mass: 88.35 (M+H⁺).

3-(1-Benzyloxy-7-chloro-isoquinolin-6-yloxy)-cyclobutylamine (51)

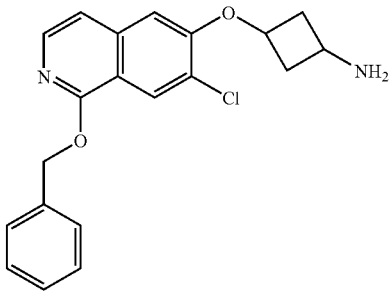 [SMILES: NC1CC(Oc2cc3ccnc(OCc4ccccc4)c3cc2Cl)C1]

To a suspension of 459 mg (11.5 mmol) of sodium hydride (60%) in 16 mL of dimethyl acetamide was added a solution of 333 mg (3.82 mmol) of 3-amino-cyclobutanol (50) in 8 ml of dimethyl acetamide. After stirring for 60 min at room temperature a solution of 1.00 g (3.48 mmol) of 1-benzyloxy-7-chloro-6-fluoro-isoquinoline (11) in 16 ml of dimethyl acetamide was added and stirring was continued first at room temperature, then for 2 h at 50° C. until the reaction went to completion. The reaction was quenched by addition of water and the reaction mixture was extracted three times with a mixture of dichloromethane and 2-propanol (3:1). The combined organic layers were evaporated, water was added and the crude product was subjected to lyophilization to remove remainders of dimethyl acetamide. The obtained crude product was purified by silica gel chromatography to yield 377 mg of the title compound (51) as a mixture of diastereoisomers. $R_t$=0.85 min (Method H). Detected mass: 355.1 (M+H⁺).

The following two products were obtained by the same procedure described for the synthesis of 51 using 1-benzyloxy-7-chloro-6-fluoro-isoquinoline (11) and the corresponding (3-amino-cyclobutyl)-methanols.

6-(3-Amino-cyclobutoxy)-7-chloro-2H-isoquinolin-1-one (54)

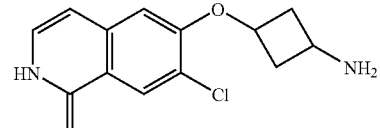

A solution of 377 mg (1.06 mmol) of 3-(1-benzyloxy-7-chloro-isoquinolin-6-yloxy)-cyclobutylamine (51) in 8 mL of 2-propanol was treated with 8 mL of 2N aqueous hydrochloric acid and stirred until complete conversion. The reaction mixture was evaporated, twice lyophilized from water and recrystallized from 2-propanol. 195 mg of the title compound could be isolated as hydrochloride as unseparable mixture of diastereoisomers. $R_t$=1.92 min (Method G). Detected mass: 265.1 (M+H⁺).

The pure cis- and trans-isomers can be accessed as hydrochlorides by the same procedure as described for the synthesis of 6-(3-amino-cyclobutoxy)-7-chloro-2H-isoquinolin-1-one (54) using the corresponding cis- or trans-isomer of 3-amino-cyclobutanol (50) respectively. cis-Isomer (54a): $R_t$=1.85 min (Method I). Detected mass: 265.1 (M+H⁺); trans-isomer (54b): $R_t$=1.90 min (Method I). Detected mass: 265.1 (M+H⁺).

cis-6-(3-Amino-cyclobutylmethoxy)-7-chloro-2H-isoquinolin-1-one (55)

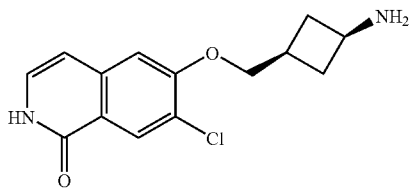 [SMILES: N[C@H]1C[C@@H](COc2cc3cc[nH]c(=O)c3cc2Cl)C1]

TABLE 5

| Example | Starting comp. | Product | Chemical Name | [M + H⁺] | $R_t$ [min] | Method |
|---|---|---|---|---|---|---|
| 52 | cis-(3-amino-cyclobutyl)-methanol | | cis-3-(1-Benzyloxy-7-chloro-iso-quinolin-6-yloxymethyl)-cyclobutylamine | 369.2 | 1.26 | C |
| 53 | trans-(3-amino-cyclobutyl)-methanol | | trans-3-(1-Benzyloxy-7-chloro-iso-quinolin-6-yloxymethyl)-cyclobutylamine | 369.2 | 1.22 | C |

Starting from 756 mg (2.05 mmol) of cis-6-(3-amino-cyclobutylmethoxy)-7-chloro-2H-isoquinolin-1-one (52), 460 mg of cis-6-(3-amino-cyclobutylmethoxy)-7-chloro-2H-isoquinolin-1-one (55) could be obtained as the hydrochloride as described for compound 54. $R_t$=1.91 min (Method I). Detected mass: 279.1 (M+H$^+$).

trans-6-(3-Amino-cyclobutyl methoxy)-7-chloro-2H-isoquinolin-1-one (56)

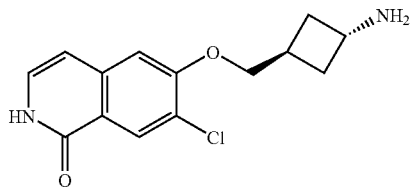 [SMILES: N[C@H]1C[C@H](COc2cc3cc[nH]c(=O)c3cc2Cl)C1]

Starting from 778 mg (2.11 mmol) of trans-6-(3-amino-cyclobutylmethoxy)-7-chloro-2H-isoquinolin-1-one (53), 353 mg of trans-6-(3-amino-cyclobutylmethoxy)-7-chloro-2H-isoquinolin-1-one (56) could be obtained as the hydrochloride as described for compound 54. $R_t$=1.87 min (Method I). Detected mass: 279.2 (M+H$^+$).

cis-5-(tert-Butyl-dimethyl-silanyloxy)-cyclooctanol (57)

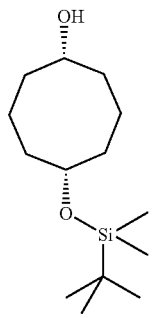 [SMILES: CC(C)(C)[Si](C)(C)O[C@H]1CCC[C@@H](O)CCC1]

21.4 g (312 mmol) of imidazole, 34.5 g (229 mmol) of t-butyldimethylsilyl chloride and 10 mg of DMAP were added to a solution of cis-1,5-cyclooctanediol in 500 mL of THF. The reaction mixture was stirred for 2 h before quenching with water followed by extraction with ethyl acetate. The organic phase was washed with saturated sodium chloride solution and dried over magnesium sulfate. Filtration and evaporation under reduced pressure gave crude product which was purified by silica gel chromatography (n-heptane/ethyl acetate, 4:1) to give 26.0 g of the desired product as a colourless oil. $R_t$=3.00 min (Method J). Detected mass: 259.2 (M+H$^+$).

5-(tert-Butyl-dimethyl-silanyloxy)-cyclooctanone (58)

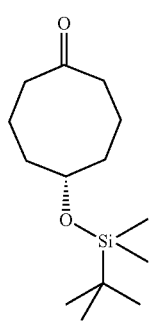

A solution of 4.5 g (58 mmol) of dimethyl sulphoxide in 25 mL dichloromethane was added dropwise to a stirred solution of 3.7 g (29 mmol) of oxalyl chloride in 50 mL of dichloromethane at −78° C. The solution was stirred for 30 minutes at −78° C. and then 5.0 g (19.3 mmol) of cis-5-(tert-butyl-dimethyl-silanyloxy)-cyclooctanol (57) in 30 mL of dichloromethane was added dropwise keeping the temperature at −78° C. After stirring for 30 minutes, 9.8 g (97 mmol) of triethylamine was added dropwise and the temperature allowed to warm to −30° C. Further 50 mL of dichloromethane were added and the solution stirred for 1 h at −30° C. With stirring 300 mL of a saturated ammonium chloride solution were added portionwise and then the organic layer was separated. After washing with further ammonium chloride solution, the organic phase was dried over magnesium sulfate, filtered and evaporated to give 5.0 g of the desired product as a yellow oil which was used without purification. $R_t$=1.96 min (Method C). Detected mass: 257.3 (M+H$^+$).

5-(tert-Butyl-dimethyl-silanyloxy)-cyclooctylamine (59)

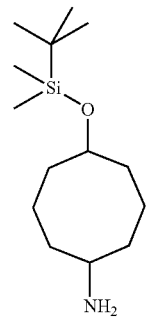 [SMILES: CC(C)(C)[Si](C)(C)OC1CCCC(N)CCC1]

11.0 g (38.6 mmol) of titanium isopropoxide were added to a solution of 5.0 g (19.3 mmol) of 5-(tert-butyl-dimethyl-silanyloxy)-cyclooctanone (58) in 48.3 mL (96.5 mmol) of a 2M solution of ammonia in ethanol and stirred for 6 hours. After addition of 1.1 g (29 mmol) of sodium borohydride the mixture was stirred at room temperature for 4 days. The reaction was quenched by addition of 50 mL of a 2M aqueous ammonia solution. A white precipitate was removed by filtration and washed with ethyl acetate. The filtrate was extracted with ethyl acetate and the combined organic layers dried over magnesium sulfate, filtered and evaporated to yield 4.5 g of 5-(tert-butyl-dimethyl-silanyloxy)-cyclooctylamine (59) as a mixture of diastereomers as a yellow oil which was used without purification. $R_t$=2.14 min (Method J). Detected mass: 258.2 (M+H$^+$).

5-Amino-cyclooctanol (60)

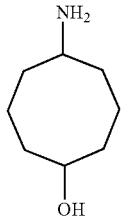

35 mL of 2N aqueous hydrochloric acid were added to a solution of 3.5 g (13.6 mmol) of 5-(tert-butyl-dimethyl-silanyloxy)-cyclooctylamine (59) in 35 mL 2-propanol and the resulting solution was stirred at room temperature overnight. The isopropanol was removed under reduced pressure and the resulting aqueous solution washed with t-butylmethylether. 2.7 g of crude 5-amino-cyclooctanol (60) was obtained by freeze-drying the aqueous layer as a diastereomeric mixture as hydrochloride which was used without further purification. $R_t$=0.18 min (Method C). Detected mass: 144.2 (M+H$^+$).

5-(1-Benzyloxy-7-chloro-isoquinolin-6-yloxy)-cyclooctylamine (61)

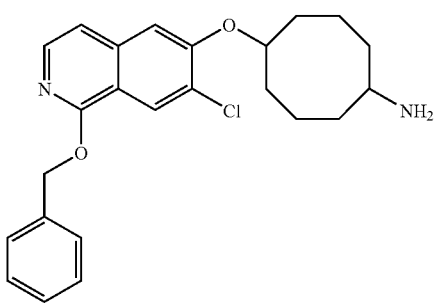 [SMILES: NC1CCCC(Oc2cc3ccnc(OCc4ccccc4)c3cc2Cl)CCC1]

1.3 g of the title compound were synthesized starting from 0.8 g (2.78 mmol) of 1-benzyloxy-7-chloro-6-fluoro-isoquinoline (11), 417 mg (14.4 mmol) of sodium hydride (60%), and 0.63 g (3.5 mmol) of 5-amino-cyclooctanol (60), following the protocol described for 3-(1-benzyloxy-7-chloro-isoquinolin-6-yloxy)-cyclobutylamine (51). Purification by silica gel chromatography (dichloromethane methanol:aq. ammonia—100:7:0.75) gave 0.35 g of the desired product as a mixture of diastereoisomers. $R_t$=1.41 min (Method C). Detected mass: 413.1 (M+H$^+$).

6-(5-Amino-cyclooctyloxy)-7-chloro-2H-isoquinolin-1-one (62)

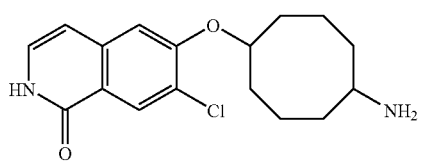 [SMILES: NC1CCCC(Oc2cc3cc[nH]c(=O)c3cc2Cl)CCC1]

Starting from 0.22 g (0.54 mmol) of 5-(1-benzyloxy-7-chloro-isoquinolin-6-yloxy)-cyclooctylamine (61), 124 mg of 6-(5-amino-cyclooctyloxy)-7-chloro-2H-isoquinolin-1-one (62) could be obtained as the hydrochloride using the method described for the preparation of compound 54. $R_t$=1.85 min (Method I). Detected mass: 321.1 (M+H$^+$).

1-Allyl-5-(tert-butyl-dimethyl-silanyloxy)-cyclooctylamine (63)

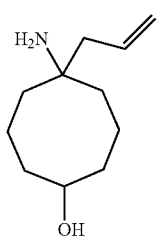

To a solution of 1.5 g (5.85 mmol) of 5-(tert-butyldimethylsilyloxy)cyclooctanone in 8.4 mL (58.5 mmol) of 7N ammonia in methanol, previously stirred for 15 min at room temperature, were added dropwise 1.7 mL (9.36 mmol) of 2-allyl-4,4,5,5-tetramethyl-1,3,2-dioxa-borolane. The reaction mixture was stirred for 18 h at room temperature. The volatiles were removed in vacuo and the residue redissolved in 100 mL of diethyl ether. Then, 100 mL of 1 N aqueous HCl were added dropwise and the resultant biphasic mixture was stirred for 30 min. The layers were separated, the aqueous layer was washed with diethyl ether and the pH adjusted to pH9 by the addition of sodium hydroxide. The suspension was then extracted with a 3:1 mixture of dichloromethane and 2-propanol and the combined organic extracts were concentrated in vacuo to afford 0.89 g of the title compound as mixture of diastereomers. $R_t$=0.44 min, 0.49 min (Method C). Detected mass: 184.3 (M+H$^+$).

5-Amino-5-propyl-cyclooctanol (64)

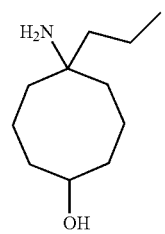

A solution of 895 mg (4.88 mmol) of 1-allyl-5-(tert-butyl-dimethyl-silanyloxy)-cyclooctylamine (63) in 15 mL of methanol was treated with 52 mg of 10% palladium on activated carbon and the mixture was stirred overnight under a hydrogen atmosphere (1 atm) at room temperature. The catalyst was removed by filtration, and the filtrate was evaporated in vacuo to give 0.794 g of the title compound (64). $R_t$=0.56 min, 0.62 min min (Method C). Detected mass: 186.3 (M+H$^+$).

5-(1-Benzyloxy-7-chloro-isoquinolin-6-yloxy)-1-propyl-cyclooctylamine (65)

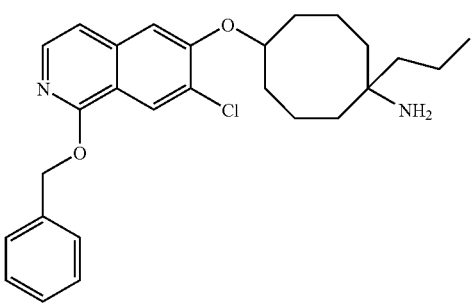 [SMILES: CCCC1(N)CCCC(Oc2cc3ccnc(OCc4ccccc4)c3cc2Cl)CCC1]

572 mg of the title compound as a mixture of diastereomers were synthesized starting from 1.11 g (3.86 mmol) of 1-benzyloxy-7-chloro-6-fluoro-isoquinoline (11), 514 mg (12.9 mmol) of sodium hydride (60%), and 794 mg (4.29 mmol) of 5-amino-5-propyl-cyclooctanol (64), following the protocol described for 3-(1-benzyloxy-7-chloro-isoquinolin-6-yloxy)-cyclobutylamine (51). $R_t$=1.52 min, 1.56 min (Method C). Detected mass: 453.3 (M+H$^+$).

6-(cis-5-Amino-5-propyl-cyclooctyloxy)-7-chloro-2H-isoquinolin-1-one and 6-(trans-5-amino-5-propyl-cyclooctyloxy)-7-chloro-2H-isoquinolin-1-one (66/67)

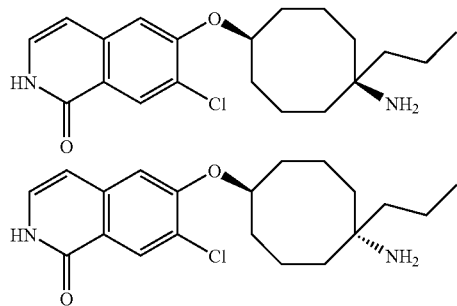

Starting from 396 mg (0.87 mmol) of 5-(1-benzyloxy-7-chloro-isoquinolin-6-yloxy)-1-propyl-cyclooctylamine (65), 6-(5-amino-5-propyl-cyclooctyloxy)-7-chloro-2H-isoquinolin-1-one could be obtained as the hydrochloride using the method described for the preparation of compound 54. 182 mg and 86 mg of the pure diastereomers 66 and 67, respectively, were obtained by separation of the mixture via preparative HPLC and lyophilization of the residues from 2N HCl and water. Stereoisomer 1 (66): $R_t$=2.31 min (Method I). Detected mass: 363.2 (M+H$^+$), 346.2 (M-NH$_3$+H$^+$). Stereoisomer 2 (67): $R_t$=2.52 min (Method G). Detected mass: 363.2 (M+H$^+$), 346.2 (M-NH$_3$+H$^+$). Relative stereochemistry of the two derivatives was assigned arbitrarily.

The following products were obtained as their hydrochlorides by the general procedure for the reductive amination reaction described for the synthesis of compounds 15-22 using the corresponding isoquinolinones and aldehydes or ketones. (Table 6)

TABLE 6

| Example | Starting compound | Aldehyde/ketone | Product | Chemical Name | [M + H$^+$] | $R_t$/[min] | Method |
|---|---|---|---|---|---|---|---|
| 68 | 66 | benzaldehyde | | 6-(5-Benzyl-amino-5-propyl-cycloocty-loxy)-7-chloro-2H-isoquinolin-1-one | 453.3 | 2.62 | I |
| 69 | 66 | acetaldehyde | | 7-Chloro-6-(5-ethylamino-5-propyl-cyclooctyloxy)-2H-isoquinolin-1-one | 391.3 | 1.06 | C |
| 70 | 54a | acetone | | 7-Chloro-6-(cis-3-isopropylamino-cyclobutoxy)-2H-isoquinolin-1-one | 307.1 | 2.06 | I |
| 71 | 54a | benzaldehyde | | 6-(3-cis-Benzyl-amino-cyclobutoxy)-7-chloro-2H-isoquinolin-1-one | 355.1 | 2.40 | I |

TABLE 6-continued

| Example | Starting compound | Aldehyde/ketone | Chemical Name | [M + H⁺] | R_f / [min] | Method |
|---|---|---|---|---|---|---|
| 72 | 54b | benzaldehyde | 6-(3-trans-Benzylaminocyclobutoxy)-7-chloro-2H-isoquinolin-1-one | 355.1 | 2.43 | I |
| 73 | 54a | Benzaldehyde | 7-Chloro-6-(3-cis-dibenzylaminocyclobutoxy)-2H-isoquinolin-1-one | 445.1 | 2.72 | I |
| 74 | 54b | Benzaldehyde | 7-Chloro-6-(3-trans-dibenzylaminocyclobutoxy)-2H-isoquinolin-1-one | 445.1 | 2.88 | I |
| 75 | 54b | Acetaldehyde | 7-Chloro-6-(3-trans-diethylaminocyclobutoxy)-2H-isoquinolin-1-one | 321.1 | 2.14 | I |

Determination of Rho Kinase Inhibition

To measure Rho-kinase inhibition, IC$_{50}$ values were determined according to the following protocol:

Active human recombinant ROCK II (N-terminal His6-tagged recombinant human ROCK-II residues 11-552) was purchased from Upstate Ltd., Dundee, UK. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-hydroxyethyl)piperazine-1-ethanesulfonic acid (Hepes), Brij-35 and dithiothreitol (DTT) were purchased from Sigma-Aldrich, Munich, Germany. Tris(hydroxymethyl)-aminomethane (Tris), magnesium chloride, NaOH, 1 M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM MgCl$_2$, 2 mM DTT, 0.02% (w/v) BSA and 3% DMSO). The ROCK II enzyme was diluted to a concentration of 100 ng/ml in buffer 2 (25 mM Tris-HCl, pH 7.4, 5 mM $MgCl_2$, 2 mM DTT and 0.02% (w/v) BSA). The peptide substrate and ATP were diluted to concentrations of 3 µM and 120 µM, respectively, in the buffer 2. 2 µl of the compound solution were mixed with 2 µl of the diluted enzyme in a 384-well small volume microtiter plate (Greiner, Bio-One, Frickenhausen, Germany), and the kinase reaction was initiated by addition of 2 µl of the solution containing peptide substrate and ATP. After 60 min incubation at 32° C., the reaction was stopped by addition of 20 µl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al. (J. Biomol. Screening 2004, 9(5), 409-416). Separation conditions were as follows: Pressure—1.3 psi, upstream voltage—1562 V, downstream voltage—500 V, sample sip time 200 ms. Positive controls (buffer 1 instead of compound) and negative controls (buffer 1 instead of compound and buffer 2 instead of ROCK II) were run in parallel on each plate.

The following products/compounds were tested in said assay by using the respective form (salt or free base) obtained as in the examples described above and the following activities were measured.

| Compound No. | pIC50 |
|---|---|
| 15 | +++++ |
| 16 | +++++ |
| 17 | +++++ |
| 18 | +++++ |
| 19 | +++++ |
| 20 | +++++ |
| 21 | +++++ |
| 22 | +++++ |
| 24 | +++++ |
| 28 | ++++ |
| 29 | ++++ |
| 30 | +++++ |
| 31 | +++++ |
| 44 | +++++ |
| 45 | +++++ |
| 47 | +++++ |
| 48 | +++++ |
| 54 | +++++ |
| 56 | +++++ |
| 66 | +++++ |
| 67 | +++++ |

The given activity is denoted as the negative decadal logarithm of the $IC_{50}$ ($pIC_{50}$) as follows:

| | |
|---|---|
| +: | $pIC_{50} \leq 3.0$ |
| ++: | $3.0 \leq pIC_{50} < 4.0$ |
| +++ | $4.0 \leq pIC_{50} < 5.0$ |
| ++++: | $5.0 \leq pIC_{50} < 6.0$ |
| +++++: | $6.0 \leq pIC_{50}$ |

The invention claimed is:
1. A compound of the formula (I)

(I)

or of the formula (I')

(I')

wherein
$R_2$ is H, halogen or $(C_1-C_6)$alkyl;
$R_3$ is
H,
halogen,
$(C_1-C_6)$alkyl,
OH,
O—R",
$NH_2$,
NHR",
NR"R" or
NH—C(O)—R",
$R_4$ is
H,
halogen,
hydroxy,
CN,
$(C_1-C_6)$alkyl,
$R_5$ is
H,
halogen,
CN,
$NO_2$,
$(C_1-C_6)$alkyl,
$(C_2-C_6)$alkenyl,
CH(OH)—$(C_1-C_6)$alkyl,
$NH_2$,
NH—$SO_2$H,
NH—$SO_2$—$(C_1-C_6)$alkyl,
NH—C(O)—$(C_1-C_6)$alkyl,
C(O)N[$(C_1-C_6)$alkyl]$_2$;
C(O)OH, or
C(O)O—$(C_1-C_6)$alkyl;
$R_6$ is H, $(C_1-C_8)$alkyl, or $(C_1-C_6)$alkylene-phenyl;
is
H,
R',
$(C_1-C_8)$alkyl,
$(C_1-C_6)$alkylene-R',
$(C_1-C_6)$alkylene-O—$(C_1-C_6)$alkyl, $(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)OR'
C(O)$(C_1-C_6)$alkyl,
C(O)R',
C(O)NH—$(C_1-C_6)$alkyl,
C(O)NHR',
C(O)N[$(C_1-C_6)$alkyl]R'
C(O)N[$(C_1-C_6)$alkyl]$_2$,
C(O)—$(C_1-C_6)$alkylene-R',
or
$R_6$ and $R_6'$, together with the N-atom to which they are attached, form a $(C_5-C_{10})$ heterocyclyl group;
$R_7$ is
H,
halogen,
CN,
NO$_2$,
$(C_1-C_6)$alkyl,
O—$(C_1-C_6)$alkyl,
$(C_2-C_6)$alkenyl,
CH(OH)—$(C_1-C_6)$alkyl,
NH$_2$,
NH—R',
NH—SO$_2$-$(C_1-C_6)$alkyl,
SO$_2$—NH$_2$,
NH—C(O)—$(C_1-C_6)$alkyl,
C(O)N[$(C_1-C_6)$alkyl]$_2$,
C(O)OH, or
C(O)O—$(C_1-C_6)$alkyl;
$R_8$ is H, halogen or $(C_1-C_6)$alkyl;
n is 1, 2, 3 or 4;
m is 1, 3, 4 or 5; and
L is O or -O—$(C_1-C_6)$alkylene;
R' is
$(C_3-C_8)$cycloalkyl,
$(C_5-C_{10})$heterocyclyl,
$(C_6-C_{10})$aryl; and
R'' is
$(C_1-C_6)$alkyl,
$(C_1-C_6)$alkylene-O—$(C_1-C_6)$alkyl, or
$(C_1-C_6)$alkylene-NR$_x$R$_y$; and
$R_x$ and $R_y$ are independently of each other
$(C_1-C_6)$alkyl,
$(C_1-C_4)$alkylene-NH$(C_1-C_6)$alkyl,
$(C_1-C_4)$alkylene-N[$(C_1-C_6)$alkyl]$_2$,
wherein in residues $R_4$, $R_5$, $R_6$, $R_6'$, $R_7$ and $R_8$ alkyl, alkylene or cycloalkyl can optionally be substituted one or more times by OH, OCH$_3$, COOH, COOCH$_3$, NH$_2$, NHCH$_3$, N(CH$_3$)$_2$, CONHCH$_3$ or CON(CH$_3$)$_2$;
wherein in residues $R_2$ to $R_8$ alkyl or alkylene can optionally be substituted one or more times by halogen;
wherein in residues $R_3$ and $R_6'$ $(C_6-C_{10})$aryl and $(C_5-C_{10})$ heterocyclyl are unsubstituted or substituted one or more times by a group independently selected from halogen, OH, NO$_2$, N$_3$, CN, C(O)—$(C_1-C_6)$alkyl, COOH, COO$(C_1-C_6)$alkyl, CONH$_2$, CONH$(C_1-C_6)$alkyl, CON[$(C_1-C_6)$alkyl]$_2$, $(C_3-C_8)$cycloalkyl, $(C_1-C_6)$alkyl, $(C_1-C_6)$alkylene-OH, $(C_1-C_6)$alkylene-NH$_2$, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, PO$_3$H$_2$, SO$_3$H, SO$_2$—NH$_2$, SO$_2$NH$(C_1-C_6)$alkyl, SO$_2$N[$(C_1-C_6)$alkyl]$_2$, S—$(C_1-C_6)$alkyl; SO—$(C_1-C_6)$alkyl, SO$_2$—$(C_1-C_6)$alkyl, SO$_2$—N=CH—N[$(C_1-C_6)$alkyl]$_2$, C(NH)(NH$_2$), NH—$(C_1-C_6)$alkyl, N[$(C_1C_6)$alkyl]$_2$, NH—C(O)—$(C_1-C_6)$alkyl, NH—C(O)O—$(C_1-C_6)$alkyl, NH—SO$_2$—$(C_1-C_6)$alkyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl]; and
wherein, if m is 3, $R_6$ is not H; and
wherein, if m is 3 and $R_6'$ is a residue selected from
$(C_1-C_8)$alkyl,
$(C_3-C_8)$cycloalkyl,
$(C_1-C_6)$alkylene-R',
$(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)NH$_2$,
$(C_1-C_6)$alkylene-C(O)NH—R', or
$(C_1-C_6)$alkylene-C(O)N[R']$_2$;
alkyl, alkylene or cycloalkyl in said residue is substituted one or more times by OH, OCH$_3$, COOH, COOCH$_3$, NH$_2$, NHCH$_3$, N(CH$_3$)$_2$, CONHCH$_3$ or CON(CH$_3$)$_2$; or
stereoisomeric form thereof and/or tautomeric form thereof and/or pharmaceutically acceptable salt thereof.

2. The compound according to claim 1, wherein $R_3$ is H, halogen, O—R'' or NHR''.

3. The compound according to claim 2, wherein $R_3$ is H or NHR''.

4. The compound according to claim 3, wherein $R_3$ is H; NH—$(C_5-C_6)$heterocyclyl, or NH-phenyl.

5. The compound according to claim 4, wherein $R_3$ is H.

6. The compound according to claim 1, wherein $R_8$ is H, halogen or $(C_1-C_4)$alkyl.

7. The compound according to claim 6, wherein $R_8$ is H, Cl, F, methyl or ethyl.

8. The compound according to claim 7, wherein $R_8$ is H.

9. The compound according to claim 1, wherein $R_4$ is H, halogen or $(C_1-C_6)$alkyl.

10. The compound according to claim 9, wherein $R_4$ is H, halogen or $(C_1-C_4)$alkyl.

11. The compound according to claim 10, wherein $R_4$ is H.

12. The compound according to claim 1, wherein $R_5$ is H, halogen, CN, or $(C_1-C_6)$alkyl.

13. The compound according to claim 12, wherein $R_5$ is H, halogen, $(C_1-C_6)$alkyl, or $(C_2-C_6)$alkenyl.

14. The compound according to claim 13, wherein $R_5$ is H, halogen, methyl, ethyl, or vinyl.

15. The compound according to claim 14, wherein $R_5$ is H, halogen, methyl, or ethyl.

16. The compound according to claim 15, wherein $R_5$ is H.

17. The compound according to claim 1, wherein $R_7$ is H, halogen, CN, $(C_1-C_6)$alkyl, O—$(C_1-C_6)$alkyl, or $(C_2-C_6)$alkenyl.

18. The compound according to claim 17, wherein $R_7$ is H, halogen, CN, $(C_1-C_4)$alkyl, O—$(C_1-C_4)$alkyl, or $(C_2-C_4)$alkenyl.

19. The compound according to claim 18, wherein $R_7$ is H, fluoro, chloro, bromo, methyl, ethyl, methoxy, or vinyl.

20. The compound according to claim 19, wherein $R_7$ is H, fluoro, chloro, bromo, methyl or methoxy.

21. The compound according to claim 20, wherein $R_7$ is H.

22. The compound according to claim 1, wherein $R_2$ is H, halogen or $(C_1-C_4)$alkyl.

23. The compound according to claim 22, wherein $R_2$ is H or $(C_1-C_2)$alkyl.

24. The compound according to claim 23, wherein $R_2$ is H, methyl or ethyl.

25. The compound according to claim 1, wherein n is 1, 2 or 3.

26. The compound according to claim 25, wherein n is 1 or 2.

27. The compound according to claim 26, wherein n is 1.

28. The compound according to claim 1, wherein $R_6$ is H, $(C_1-C_6)$alkyl, or $(C_1-C_6)$alkylene-phenyl;
is
H,
$(C_1-C_6)$alkyl,
R',
$(C_1-C_4)$alkylene-$(C_3-C_8)$cycloalkyl,
$(C_1-C_4)$alkylene-$(C_5-C_{10})$heterocyclyl,
$C_1-C_4)$alkylene-$(C_6-C_{10})$aryl,
$(C_1-C_6)$alkylene-O—$(C_1-C_6)$alkyl,
$(C_1-C_4)$alkylene-C(O)—$(C_5-C_{10})$heterocyclyl,
$(C_1-C_4)$alkylene-C(O)—$(C_6-C_{10})$aryl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)($C_1-C_6$)alkyl,
C(O)R'
C(O)NH—$(C_1-C_6)$alkyl,
C(O)N[$(C_{1-6})$alkyl]$_2$, or
C(O)$(C_1-C_6)$alkylene-R',
or $R_6$ and $R_6'$, together with the N-atom to which they are attached, form a $(C_5-C_{10})$heterocyclyl group.

29. The compound according to claim 28, wherein $R_6$ is H, $(C_1-C_6)$alkyl, or $(C_1-C_6)$alkylene-phenyl;
is
H,
$(C_1-C_6)$alkyl,
$(C_5-C_{10})$heterocyclyl,
$(C_3-C_8)$cycloalkyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)$(C_1-C_6)$alkyl,
C(O)$(C_3-C_8)$cycloalkyl,
C(O)NH—$(C_1-C_6)$alkyl,
C(O)N[$(C_1-C_6)$alkyn]$_2$,
C(O)$(C_1-C_6)$alkylene-$(C_3-C_8)$cycloalkyl,
C(O)$(C_1-C_6)$alkylene-$(C_5-C_{10})$heterocyclyl,
C(O)$(C_1-C_6)$alkylene-$(C_6-C_{10})$aryl,
or $R_6$ and $R_6'$, together with the N-atom to which they are attached form a $(C_5-C_{10})$heterocyclyl group.

30. The compound according to claim 29, wherein
$R_6$ is H, $(C_1-C_6)$alkyl, and $R_6'$ is H,
$(C_1-C_6)$alkyl,
$(C_3-C_8)$cycloalkyl,
$(C_5-C_{10})$heterocyclyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)O—$(C_1-C_6)$alkyl,
C(O)$(C_1-C_6)$alkyl,
C(O)$(C_3-C_8)$cycloalkyl,
C(O)NH—$(C_1-C_6)$alkyl,
C(O)N[$(C_1-C_6)$alkyl]$_2$,
C(O)$(C_1-C_6)$alkylene-$(C_3-C_8)$cycloalkyl,
C(O)$(C_1-C_6)$alkylene-$(C_5-C_{10})$heterocyclyl,
C(O)$(C_1-C_6)$alkylene-$(C_6-C_{10})$aryl, or
$R_6$ and $R_6'$, together with the N-atom to which they are attached, form a $(C_5-C_{10})$heterocyclyl group.

31. The compound according to claim 30, wherein
$R_6$ is H or $(C_1-C_6)$alkyl and
$R_6'$ is H,
$(C_1-C_6)$alkyl,
$(C_3-C_8)$cycloalkyl,
$(C_6-C_{10})$aryl,
$(C_5-C_{10})$heterocyclyl,
$(C_1-C_4)$alkylene-$(C_3-C_8)$cycloalkyl,
$(C_1-C_4)$alkylene-$(C_5-C_{10})$heterocyclyl,
$(C_1-C_6)$alkylene-$(C_6-C_{10})$aryl,
$(C_1-C_4)$alkylene-O—$(C_1-C_4)$alkyl,
$(C_1-C_4)$alkylene-C(O)N[$(C_1-C_4)$alkyl]$_2$,
$(C_1-C_6)$alkylene-C(O)NH—$(C_1-C_6)$alkyl,
C(O)$(C_1-C_6)$alkyl,
C(O)$(C_1-C_6)$alkylene-$(C_5-C_{10})$heterocyclyl, or
$R_6$ and $R_6'$, together with the N-atom to which they are attached, form a $(C_5-C_{10})$heterocyclyl group.

32. The compound according to claim 31, wherein
$R_6$ is H, $(C_1-C_6)$alkyl and
$R_6'$ is H;
$(C_1-C_6)$alkyl;
$(C_3-C_8)$cycloalkyl;
$(C_1-C_4)$alkylene-$(C_3-C_8)$cycloalkyl;
$(C_1-C_4)$alkylene-O—$(C_1-C_4)$alkyl;
C(O)$(C_1-C_4)$alkyl;
$(C_1-C_4)$alkylene-(C(O)N[$(C_1-C_4)$alkyl]$_2$;
$(C_1-C_4)$alkylene-$(C_5-C_{10})$heterocyclyl wherein heterocyclyl is unsubstituted or substituted one or more times by a group independently selected from $(C_1-C_4)$alkyl, O—$(C_1-C_4)$alkyl, halogen, or phenyl or is substituted once by $(C_5-C_6)$heterocyclyl, wherein phenyl or $(C_5-C_6)$heterocyclyl is unsubstituted or substituted one to three times by a group independently selected from halogen, $(C_1-C_4)$alkyl or O—$(C_1-C_4)$alkyl;
$(C_1-C_4)$alkylene-$(C_6-C_{10})$aryl wherein aryl is unsubstituted or substituted one or more times by a group independently selected from halogen, $(C_1-C_4)$alkyl, O—$(C_1-C_4)$alkyl, CN, SO$_2$—NH$_2$,
SO$_2$—$(C_1-C_4)$alkyl, SO$_2$—N=CH—N[$(C_1-C_4)$alkyl]$_2$, NH—CO—$(C_1-C_4)$alkyl, CO—O—$(C_1-C_4)$alkyl, or is substituted once by unsubstituted phenyl, unsubstituted O-phenyl or unsubstituted $(C_5-C_6)$heterocyclyl;
C(O)$(C_1-C_6)$alkyl;
C(O)$(C_1-C_6)$alkylene-$(C_5-C_{10})$heterocyclyl;
or $R_6$ and $R_6'$, together with the N-atom to which they are attached, form a $(C_5-C_6)$heterocyclyl group, which is unsubstituted or substituted one to three times by $(C_1-C_4)$alkyl or C(O)O$(C_1-C_4)$alkyl;
wherein a $(C_1-C_6)$alkyl or $(C_1-C_4)$ alkyl residue is unsubstituted or substituted one to three times by halogen.

33. The compound according to claim 32, wherein $R_6$ is H, $(C_1-C_6)$alkyl and $R_6'$ is H, $(C_1-C_6)$alkyl or $(C_3-C_8)$cycloalkyl.

34. The compound according to claim 33, wherein $R_6$ is H and $R_6'$ is H, $(C_1-C_6)$alkyl or $(C_3-C_8)$cycloalkyl.

35. The compound according to claim 34, wherein $R_6$ and $R_6'$ are H.

36. The compound according to claim 1, wherein m is 3 and L is attached to the 3-position or to the 4-position of the amino cyclohexane ring.

37. The compound according to claim 1, wherein m is 3 and L is attached to the 4-position of the amino cyclohexane ring.

38. The compound according to claim 1, wherein L is O-methylene, O-ethylene or O.

39. The compound according to claim 1, wherein L is O.

40. The compound according to claim 1, wherein
$R_3$ is H, halogen, $(C_1-C_4)$alkylene-R', O—R" or NHR";
$R_4$ is H, halogen or $(C_1-C_6)$alkyl;
$R_5$ is H, $(C_1-C_6)$alkyl, halogen, CN, or $(C_2-C_6)$alkeny;
$R_6$ is H, $(C_1-C_8)$alkyl, or $(C_1-C_6)$alkylene-phenyl;
is H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)NH$_2$, $(C_1-C_6)$alkylene-C(O)NH—R', $(C_1-C_6)$alkylene-C(O)N[$(C_1-C_4)$alkyl]$_2$, $(C_1-C_6)$alkylene-C(O)N[R']$_2$, C(O)$(C_1-C_6)$alkyl, C(O)$(C_3-C_8)$cycloalkyl, C(O)$(C_5-C_{10})$heterocyclyl, C(O)NH—$(C_1-C_6)$alkyl, C(O)N[$(C_1-C_6)$alkyl]$_2$, C(O)$(C_1-C_6)$alkylene-$C_3-C_8$)cycloalkyl, C(O)$(C_1-C_6)$alkylene-$(C_5-C_{10})$heterocyclyl, C(O)$(C_1-C_6)$alkylene-$(C_6-C_{10})$aryl,
or $R_6$ and $R_6$', together with the N-atom to which they are attached, form a $(C_5-C_6)$heterocyclyl group;
$R_7$ is H, halogen, CN, $(C_1-C_6)$alkyl, O—$(C_1-C_6)$alkyl, or $(C_2-C_6)$alkenyl;
m is 3
n is 1, 2 or 3, and
L is O, O-methylene or O-ethylene.

41. The compound according to claim 1, wherein
$R_2$ is H or $(C_1-C_4)$alkyl;
$R_3$ is H, halogen or NHR";
$R_4$ is H, halogen or $(C_1-C_4)$alkyl;
$R_5$ is H, $(C_1-C_6)$alkyl, halogen, or $(C_2-C_4)$alkenyl;
$R_6$ is H, $(C_1-C_8)$alkyl, or $(C_1-C_6)$alkylene-phenyl;
is H, $(C_3-C_8)$cycloalkyl, $(C_1-C_8)$alkyl, $(C_1-C_6)$alkylene-O—$(C_1-C_6)$alkyl, $(C_1-C_3)$alkylene-R', C(O)$(C_1-C_6)$alkyl, C(O)$(C_3-C_8)$cycloalkyl, C(O)$(C_5-C_6)$heterocyclyl, C(O)$(C_1-C_6)$alkylene-$(C_3-C_8)$cycloalkyl, C(O)$(C_1-C_6)$alkylene-$(C_5-C_6)$heterocyclyl or C(O)$(C_1-C_6)$alkylene-$(C_6-C_{10})$aryl;
$R_7$ is H, halogen, CN, $(C_1-C_6)$alkyl, O—$(C_1-C_6)$alkyl, or $(C_2-C_6)$alkenyl;
$R_8$ is H, halogen or $(C_1-C_6)$alkyl;
m is 3
n is 1, 2 or 3; and
L is O.

42. The compound according to claim 1, wherein
$R_2$ is H or $(C_1-C_4)$alkyl;
$R_3$ is H, NH—$(C_5-C_6)$heteroaryl or NH-phenyl;
$R_4$ is H, halogen or $(C_1-C_4)$alkyl;
$R_5$ is H, $(C_1-C_4)$alkyl, halogen, or $(C_2-C_4)$alkenyl;
$R_6$ is $(C_1-C_4)$alkyl;
$R_6$' is H, $(C_3-C_8)$cycloalkyl, $(C_1-C_8)$alkyl, $(C_1-C_3)$alkylene-R'; C(O)$(C_1-C_6)$alkyl, C(O)$(C_3-C_6)$cycloalkyl, C(O)$(C_5-C_6)$heterocyclyl, C(O)$(C_1-C_3)$alkylene-$(C_3-C_6)$cycloalkyl, C(O)$(C_1-C_3)$alkylene-$(C_5-C_6)$heterocyclyl, or C(O)$(C_1-C_3)$alkylene-phenyl;
$R_7$ is H, halogen, CN, $(C_1-C_4)$alkyl, O—$(C_1-C_4)$alkyl, or $(C_2-C_4)$alkenyl;
$R_8$ is H, halogen or $(C_1-C_4)$alkyl;
m is 3
n is 1; and
L is O.

43. A compound selected from the group consisting of
1-[4-(7-Chloro-1-oxo-1,2-dihydro-isoquinolin-6-yloxy)-cyclohexyl]-piperidine-4-carboxylic acid amide,
7-Chloro-6-(4-piperidin-1-yl-cyclohexyloxy)-2H-isoquinolin-1-one,
7-Chloro-6-(4-morpholin-4-yl-cyclohexyloxy)-2H-so-quinolin-1-one,
7-Chloro-6-(4-pyrrolidin-1-yl-cyclohexyloxy)-2H-isoquinolin-1-one,
7-Chloro-6-[4-(4-methyl-piperazin-1-yl)-cyclohexyloxy]-2H-isoquinolin-1-one,
[4-(7-Chloro-1-oxo-1,2-dihydro-isoquinolin-6-yloxy)-cis-cyclohexylamino]-acetic acid ethyl ester,
[4-(7-Chloro-1-oxo-1,2-dihydro-isoquinolin-6-yloxy)-cis-cyclohexylamino]-acetic acid,
7-Methyl-6-(4-pyrrolidin-1-yl-cyclohexyloxy)-2H-isoquinolin-1-one,
N-[4-(7-Methyl-1-oxo-1,2-dihydro-isoquinolin-6-yloxy)-trans-cyclohexyl]-3-piperidin-4-yl-propionamide,
N-[4-(7-Methyl-1-oxo-1,2-dihydro-isoquinolin-6-yloxy)-trans-cyclohexyl]-2-piperidin-4-yl-acetamide,
N-[4-(7-Chloro-1-oxo-1,2-dihydro-isoquinolin-6-yloxy)-cis-cyclohexyl]-3-piperidin-4-yl-propionamide,
N-[4-(7-Chloro-1-oxo-1,2-dihydro-isoquinolin-6-yloxy)-cis-cyclohexyl]-2-piperidin-4-yl-acetamide,
6-((1S,3S)-3-Amino-cyclopentyloxy)-2H-isoquinolin-1-one,
6-((1S,3S)-3-Amino-cyclopentyloxy)-7-chloro-2H-isoquinolin-1-one,
6-((1S,3R)-3-Amino-cyclopentyloxy)-2H-isoquinolin-1-one,
6-((1S,3R)-3-Amino-cyclopentyloxy)-7-chloro-2H-isoquinolin-1-one,
6-((cis-4-Amino-cycloheptyloxy)-7-methyl-2H-isoquinolin-1-one, and
7-Chloro-6-(cis-4-Amino-cycloheptyloxy)-2H-isoquinolin-1-one, or stereoisomeric form thereof and/or pharmaceutically acceptable salt thereof.

44. A compound selected from the group consisting of
6-(cis-4-Amino-cycloheptyloxy)-2H-isoquinolin-1-one,
6-(3-Amino-cyclobutoxy)-7-chloro-2H-isoquinolin-1-one,
cis-6-(3-Amino-cyclobutylmethoxy)-7-chloro-2H-isoquinolin-1-one,
trans-6-(3-Amino-cyclobutylmethoxy)-7-chloro-2H-isoquinolin-1-one,
6-(5-Amino-cyclooctyloxy)-7-chloro-2H-isoquinolin-1-one,
5-(1-Benzyloxy-7-chloro-isoquinolin-6-yloxy)-1-propyl-cyclooctylamine,
6-(5-Amino-5-propyl-cyclooctyloxy)-7-chloro-2H-isoquinolin-1-one,
6-(5-Benzyl-amino-5-propyl-cyclo-octyloxy)-7-chloro-2H-isoquinolin-1-one,
7-Chloro-6-(5-ethylamino-5-propyl-cyclooctyloxy)-2H-isoquinolin-1-one,
7-Chloro-6-(cis-3-isopropylamino-cyclobutoxy)-2H-isoquinolin-1-one,
6-(3-cis-Benzylamino-cyclobutoxy)-7-chloro-2H-isoquinolin-1-one,
6-(3-trans-Benzylamino-cyclobutoxy)-7-chloro-2H-isoquinolin-1-one,
7-Chloro-6-(3-cis-dibenzylamino-cyclobutoxy)-2H-isoquinolin-1-one,
7-Chloro-6-(3-trans-dibenzylamino-cyclobutoxy)-2H-isoquinolin-1-one and 7-Chloro-6-(3-trans-diethylamino-cyclobutoxy)-2H-isoquinolin-1-one, or stereoisomeric form thereof and/or pharmaceutically acceptable salt thereof.

45. A pharmaceutical composition comprising a pharmaceutically effective amount of at least one compound according to claim 1 and/or a pharmacologically acceptable salt thereof, and physiologically tolerated excipient or carriers, and optionally one or more additives and/or one or more other active ingredients.

46. A pharmaceutical composition comprising a pharmaceutically effective amount of at least one compound according to claim 43 and/or a pharmacologically acceptable salt thereof, and physiologically tolerated excipient or carriers, and optionally one or more additives and/or one or more other active ingredients.

47. A pharmaceutical composition comprising a pharmaceutically effective amount of at least one compound according to claim 44 and/or a pharmacologically acceptable salt thereof, and physiologically tolerated excipient or carriers, and optionally one or more additives and/or or more other active ingredients.

* * * * *